United States Patent
Osborne et al.

(10) Patent No.: US 10,034,827 B2
(45) Date of Patent: *Jul. 31, 2018

(54) SKIN CARE PRODUCT AND METHOD OF USE

(71) Applicant: The Procter & Gamble Company, Cincinnati, OH (US)

(72) Inventors: Rosemarie Osborne, Cincinnati, OH (US); Matthew James McIldowie, Perth (AU); Jeffrey David Edwards, Perth (AU)

(73) Assignee: The Procter & Gamble Company, Cincinnati, OH (US)

( * ) Notice: Subject to any disclaimer, the term of this patent is extended or adjusted under 35 U.S.C. 154(b) by 231 days.

This patent is subject to a terminal disclaimer.

(21) Appl. No.: 14/857,010

(22) Filed: Sep. 17, 2015

(65) Prior Publication Data
US 2016/0074302 A1    Mar. 17, 2016

Related U.S. Application Data

(60) Provisional application No. 62/051,783, filed on Sep. 17, 2014.

(51) Int. Cl.
*A61K 8/64* (2006.01)
*A61Q 19/08* (2006.01)
(Continued)

(52) U.S. Cl.
CPC ............. *A61K 8/64* (2013.01); *A61Q 19/00* (2013.01); *A61Q 19/008* (2013.01); *A61Q 19/08* (2013.01);
(Continued)

(58) Field of Classification Search
None
See application file for complete search history.

(56) References Cited

U.S. PATENT DOCUMENTS 5,991,961 A    11/1999   Zurik
6,564,093 B1    5/2003   Ostrow
(Continued)

FOREIGN PATENT DOCUMENTS

WO    WO2006/097785    9/2006
WO    WO2011/046018    4/2011
(Continued)

OTHER PUBLICATIONS

International Search Report PCT/US2015/050625; dated Dec. 8, 2015; 12 pages.
(Continued)

*Primary Examiner* — Marcela M Cordero Garcia
*Assistant Examiner* — Jia-Hai Lee
(74) *Attorney, Agent, or Firm* — John G. Powell

(57) ABSTRACT

A cosmetic skin care product that includes an applicator and a skin care composition. The applicator includes a uni-directional magnetic array with a pitch of between 1.7 and 2.5 and a magnetic field strength of between about 24.0 and 36.0 mT. The skin care composition includes palmitoyl-lysine-threonine-threonine-lysine-serine and a dermatologically acceptable carrier. The magnetic array is tailored to enhance penetration of the Pal-KTTKS into skin during application of the skin care composition. The applicator may include a second magnetic array juxtaposed on a first magnetic array to form a bi-directional array that enhances penetration of the Pal-KTTKS into skin.

16 Claims, 14 Drawing Sheets

(51) Int. Cl.
    *B65B 63/00*     (2006.01)
    *A61Q 19/00*     (2006.01)

(52) U.S. Cl.
    CPC .......... *B65B 63/00* (2013.01); *A61K 2800/47* (2013.01); *A61K 2800/78* (2013.01); *A61K 2800/87* (2013.01)

(56) References Cited

U.S. PATENT DOCUMENTS

| | | |
|---|---|---|
| 7,608,035 B2 | 10/2009 | Farone |
| 8,019,412 B2 | 9/2011 | Edwards |
| 8,105,228 B2 | 1/2012 | Holcomb |
| 8,316,862 B2 | 11/2012 | Shapiro |
| 9,463,330 B2 * | 10/2016 | Edwards ............... A61M 37/00 |
| 2006/0222689 A1 | 10/2006 | Liu |
| 2006/0275237 A1 * | 12/2006 | Bissett ............... A61K 31/7008 424/70.13 |
| 2007/0053858 A1 | 3/2007 | Bissett |
| 2009/0093669 A1 | 4/2009 | Farone |
| 2012/0130150 A1 | 5/2012 | Edwards |
| 2012/0149969 A1 | 6/2012 | Holcomb |
| 2013/0137063 A1 | 5/2013 | Edwards |
| 2013/0144109 A1 | 6/2013 | Edwards |
| 2014/0336616 A1 | 11/2014 | Edwards |
| 2015/0150599 A1 | 6/2015 | Matsushita |

FOREIGN PATENT DOCUMENTS

| | | | |
|---|---|---|---|
| WO | WO2011/146977 A1 | 12/2011 | |
| WO | WO2011156869 A1 * | 12/2011 | ............ A61M 37/00 |
| WO | WO2012/031335 A1 | 3/2012 | |

OTHER PUBLICATIONS

International Search Report PCT/US2015/050645; dated Dec. 7, 2015.

International Search Report PCT/US2015/050641; dated Dec. 7, 2015; 8 pages.

* cited by examiner

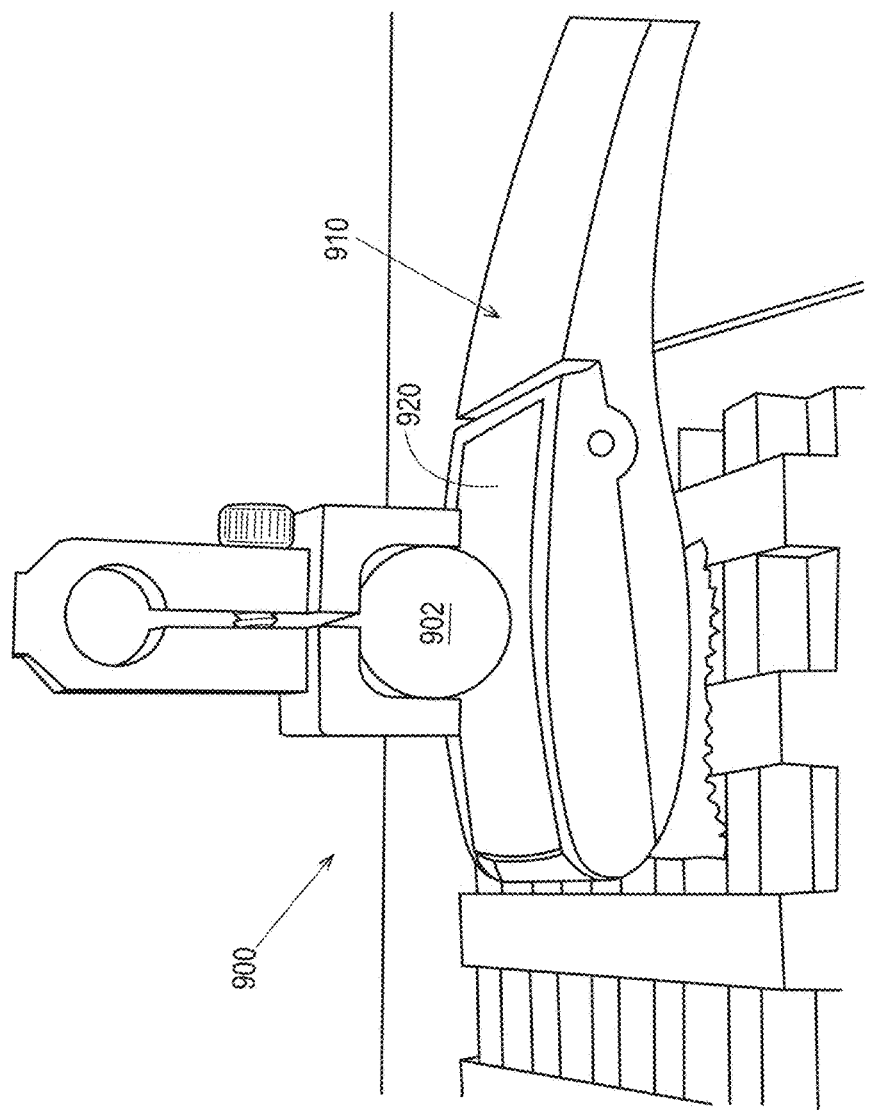

SKIN CARE PRODUCT AND METHOD OF USE

FIELD

The present invention relates generally to skin care products that provide enhanced penetration of a skin care active into skin. More specifically, the present invention relates to pairing of an applicator comprising a magnetic array and a skin care composition including skin care actives that have particular diamagnetic properties.

BACKGROUND

Topical skin care compositions containing actives that provide benefits to skin are well known. It also known that the skin health and appearance benefits provided by a cosmetic skin care active may be improved when the active can penetrate deeper into the skin. For example, peptides (e.g., di-, tri-, tetra- and pentapeptides) and their derivatives, which are known for use in regulating a variety of skin conditions, typically need to penetrate skin to provide the desired benefit. In one particular example, the peptide derivative palmitoyl-lysine-threonine-threonine-lysine-serine, also known as Pal-KTTKS (SEQ ID NO: 1), is used in skin care compositions to improve the signs of skin aging. It is believed, without being limited by theory, that Pal-KTTKS (SEQ ID NO: 1) stimulates collagen production in the dermal fibroblasts, which are the skin cells primarily responsible for collagen production, resulting in a reduction of the appearance of fine, lines and wrinkles. However, to reach the dermal fibroblasts, the Pal-KTTKS (SEQ ID NO: 1) must penetrate through the epidermal layers of the skin. Thus, it would be desirable to find a suitable way to improve the skin penetration of cosmetic skin care actives such as Pal-KTTKS (SEQ ID NO: 1).

However, effective delivery of skin care actives, such as Pal-KTTKS (SEQ ID NO: 1), into skin is an ongoing challenge. It is not uncommon for skin care actives to be introduced to skin via topical application of, for example, creams, lotions and essences. However, the actual and perceived benefits of skin care actives such as Pal-KTTKS (SEQ ID NO: 1) are largely dependent on the amount of skin care active that penetrates the top layer of skin and the depth to which it penetrates. There are various factors that limit the amount of active agent that can penetrate skin, and at present there is little control over the positioning and residency of the active agents following penetration into skin.

The amount of active agent provided in a skin care composition can be increased in various ways, for example, by increasing the amount of active agent in the skin care composition. However, this often leads to compositions that do not have a good sensory feel, increased formulation challenges, stability issues and increased manufacturing costs.

One approach to improving the efficacy of a skin care active is to use chemical penetration enhancers to facilitate changes in skin permeability, allowing enhanced penetration of the skin care active. However, the use of chemical penetration enhancers can be problematic due to unknown interaction with the active agent and the potential for adverse side effects such as irritation of skin and mucosal surfaces.

Mechanical approaches to increasing skin penetration of actives have also been explored. For example, one such approach known as iontophoresis utilizes an electrical energy gradient to accelerate a charged active agent(s) across the skin (or other barrier). An example of a device that uses iontophoresis is described in U.S. Pat. No. 7,137,965. However, iontophoresis is only suitable for specific active agents with certain ionic structures and can be injurious to certain dermal barriers due to exchange ion degradation. Additionally, iontophoresis requires the use of intimate electrical contact and adhesive electrodes, which are not suitable for all target surfaces or barriers.

Other techniques for creating mobility and/or direction in the movement of active agent(s) include magnetokinetics and magnetophoresis. However, these techniques have been difficult to implement due to poor performance, high hardware and energy requirements, and cost. An example of a device that utilizes magnetophoresis is described in US 2009/0093669. While these methods claim to increase the amount of penetration of skin care actives into skin, they still do not provide enhanced penetration in a controlled manner—both in terms of amount of penetration and depth of penetration.

In another example of a device design to effectively deliver skin care actives, WO 2011/156869 discloses a method of delivering a skin care agent through a dermal barrier using one or more displaced dipolar magnetic elements. However, this method still does not provide a targeted approach that takes account of the unique properties and targeted benefit areas in skin of different skin care actives.

Accordingly, there is a need to provide a cosmetic product that can provide improved penetration of specific cosmetic actives into skin in a controlled manner.

SUMMARY

A cosmetic skin care product comprising an applicator and a magnetic array is disclosed herein. The magnetic array comprises a first layer of one or more dipolar pairs of alternating magnetic poles with a pitch of between 1.7 mm and 2.5 mm and an overall magnetic field strength of the first layer of between 24 mT and 30 mT. The skin care composition comprises an effective amount of a skin care active with a diamagnetic susceptibility of between about −400 and −600 (e.g., Pal-KTTKS (SEQ ID NO: 1)) and a dermatologically acceptable carrier. In some instances, the present skin care product may include one or more of the following features in any combination: a magnetic array with a thickness of between 0.8 and 1.2 mm, or about 1.1 mm; a magnetic array with a pitch of between about 1.9 and 2.3 mm, or about 2.1 mm; a magnetic array that enhances delivery of the Pal-KTTKS (SEQ ID NO: 1) (e.g., at least 1.5×, at least 2.5×, at least 3.5×, at least 4× or even at least 5×) according to the Tape Stripping method; a magnetic array that enhances delivery of the Pal-KTTKS (SEQ ID NO: 1) as measured in tape strips 2 to 10, tape strips 4 to 10, tape strips 6 to 10 or even tape strips 8 to 10; a magnetic array that includes a plurality of dipolar magnetic elements arranged in pairs to form an alternating pattern of magnetic polarities (e.g., a pole of a first dipole pair is adjacent a pole of a second dipole pair of the same polarity); a magnetic array that comprises a ferromagnetic material (e.g., iron, iron containing materials, cobalt, cobalt containing materials, strontium, strontium containing materials, barium, barium containing materials, nickel, nickel containing materials, alloys and oxides of these and combinations thereof); a magnetic array that comprises boron, carbon, silicon, phosphorous, aluminum, neodymium and/or samarium; an applicator comprising a cover that covers a skin facing surface of the applicator; an applicator that comprises a cover that has a surface with a dry coefficient of friction at least 10% less than the skin facing surface of the applicator; an applicator that comprises a cover that has a surface with a wet coefficient of friction that is at least 2 times less than the skin facing surface of the applicator; a magnetic applicator and a skin care composition packaged together in a single package; a magnetic applicator and a skin care composition that are package separately and the separate packages are joined to one another; a magnetic array comprising about 12 poles per 25.4 mm; a first uni-directional magnetic array is juxtaposed on a second uni-directional magnetic array to form a bi-directional magnetic array, and the second magnetic array has a pitch and a magnetic field strength that are both less than or equal to the pitch and magnetic field strength of the first magnetic array (e.g., the second magnetic array has a pitch of between 0.8 and 1.3 and a magnetic field strength of between about 1 and 20 mT); a second magnetic array that has a thickness of between about 0.005 mm and 0.5 mm; and/or a first magnetic array angularly offset from a second magnetic array, for example, by about 90 degrees.

Also disclosed is a method of enhancing the delivery of Pal-KTTKS (SEQ ID NO: 1) to a target portion of skin in need of treatment, comprising: identifying a target portion of skin in need of treatment; applying a skin care composition to the target portion of skin, wherein the skin care composition comprises an effective amount of Pal-KTTKS (SEQ ID NO: 1) and a dermatologically acceptable carrier; and contacting the skin care composition with an applicator comprising one of the magnetic arrays disclosed herein above.

The magnetic arrays herein are designed to work in conjunction with the specific diamagnetic properties of Pal-KTTKS (SEQ ID NO: 1). The overall magnetic field strength of the magnetic array determines the amount of repulsive force induced in the Pal-KTTKS (SEQ ID NO: 1) and, as a consequence, the depth within skin to which it is driven, while the pitch of the magnetic poles determines the overall profile of the magnetic field. Use of such a magnetic array together with a composition containing Pal-KTTKS (SEQ ID NO: 1) enhances the amount of Pal-KTTKS (SEQ ID NO: 1) that: a) penetrates into a user's skin and b) is positioned at a layer of skin where it is likely to be most effective.

BRIEF DESCRIPTION OF THE DRAWINGS

FIG. 8 illustrates the test setup for the Coefficient of Friction Method.

DETAILED DESCRIPTION

Sequence Listing

Figure 1A:
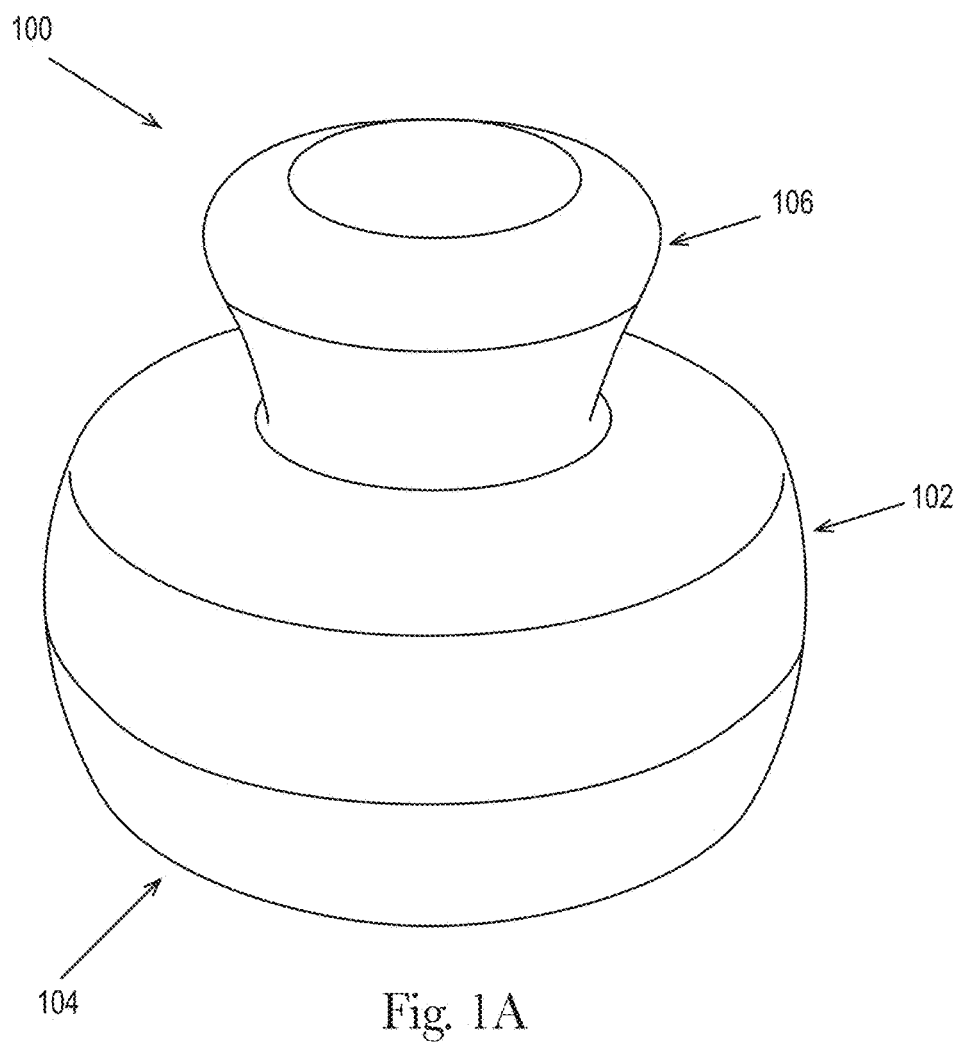
FIGS. 1A to 1D are perspective views of applicators of the skin care product described herein.

A sequence listing that sets forth the amino acid sequence for SEQ ID NO: 1 herein is on file as an ASCII text file titled "13538M_seq_list_ST25." This ASCII text file was created on Apr. 16, 2018 and is 4.28 KB in size. In accordance with MPEP § 605.08 and 37 CFR § 1.52(e), the subject matter in the ASCII text file is incorporated herein by reference.

The skin care products disclosed herein exploit the unique diamagnetic property of Pal-KTTKS (SEQ ID NO: 1) to enhance penetration of this active into skin. Diamagnetism is the property of an object or material which causes it to create a magnetic field in opposition to an externally applied magnetic field, thus causing a repulsive effect. Surprisingly, it has been discovered that by pairing a specifically tailored magnetic array with Pal-KTTKS (SEQ ID NO: 1), penetration of the active into skin can be enhanced in a controllable way. Utilizing this discovery, it is possible to provide a cosmetic skin care product in which Pal-KTTKS (SEQ ID NO: 1) and/or other skin care actives are delivered into skin to the point where they can provide a better skin care benefit than conventional skin care products.

Definitions

"About" when used in the context of a parameter or range means a value that is within 30% of the stated value (e.g., with 25%, 20%, 15%, 10%, 5%, 2% or even within 1%).

"Apply" or "application," as used in reference to a composition, means to apply or spread the composition onto a surface of keratinous tissue.

"Derivative" refers to a molecule similar to that of another one, but differing from it in respect of a certain functional moiety. Derivatives may be formed by known reactive pathways. Suitable functional moieties include esters, ethers, amides, amines, carboxylic acids, hydroxyls, halogens, thiols, and/or salt derivatives of the relevant molecule. Peptide derivatives include peptides joined to another moiety such as a fatty acid chain.

"Disposed" refers to an element being located in a particular place or position relative to another element.

"Joined" means configurations whereby an element is directly secured to another element by affixing the element directly to the other element, and configurations whereby an element is indirectly secured to another element by affixing the element to intermediate member(s) that in turn are affixed to the other element.

"Keratinous tissue" refers to keratin-containing layers disposed as the outermost protective covering of mammals which includes, but is not limited to, skin, hair, nails, cuticles, etc.

"Magnetic field" and "magnetic flux density" are used interchangeably herein and refer to the vector field measured in teslas.

"Magnetic material" means a material that can be made into a permanent magnet.

"Permanent magnet" means a magnetic material that has been magnetized such that it produces its own persistent magnetic field without the use of an electrical power source.

"Pole" refers to the portion of a magnet that exhibits a higher magnetic flux density than the adjacent regions of the magnet. For example, a conventional bar magnet has 2 poles disposed at opposite ends where the magnetic flux density is highest.

"Regulating skin condition" means improving skin appearance and/or feel, for example, by providing a benefit, such as a smoother appearance and/or feel. Herein, "improving skin condition" means effecting a visually and/or tactilely perceptible positive change in skin appearance and feel. The benefit may be a chronic or acute benefit and may include one or more of the following: reducing the appearance of wrinkles and coarse deep lines, fine lines, crevices, bumps, and large pores; thickening of keratinous tissue (e.g., building the epidermis and/or dermis and/or sub-dermal layers of the skin, and where applicable the keratinous layers of the nail and hair shaft, to reduce skin, hair, or nail atrophy); increasing the convolution of the dermal-epidermal border (also known as the rete ridges); preventing loss of skin or hair elasticity, for example, due to loss, damage and/or inactivation of functional skin elastin, resulting in such conditions as elastosis, sagging, loss of skin or hair recoil from deformation; reduction in cellulite; change in coloration to the skin, hair, or nails, for example, under-eye circles, blotchiness (e.g., uneven red coloration due to, for example, rosacea), sallowness, discoloration caused by hyperpigmentation, etc.

"Safe and effective amount" means an amount of a compound or composition sufficient to significantly induce a positive benefit, preferably a positive skin or feel benefit, including independently or in combinations the benefits disclosed herein, but low enough to avoid serious side effects (i.e., to provide a reasonable benefit to risk ratio, within the scope of sound judgment of the skilled artisan).

"Signs of skin aging" include, but are not limited to, all outward visibly and tactilely perceptible manifestations, as well as any macro- or micro-effects, due to keratinous tissue aging. These signs may result from processes which include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin.

"Skin" means the outermost protective covering of mammals that is composed of cells such as keratinocytes, fibroblasts and melanocytes. Skin includes an outer epidermal layer and an underlying dermal layer. Skin may also include hair and nails as well as other types of cells commonly associated with skin, such as, for example, myocytes, Merkel cells, Langerhans cells, macrophages, stem cells, sebocytes, nerve cells and adipocytes.

"Skin care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity; improve skin hydration; improve skin condition; and improve cell metabolism).

"Skin care composition" means a composition that includes a skin care active and regulates and/or improves skin condition.

"Skin care product" as used herein refers to a product that includes a skin care composition. Some nonlimiting examples of "skin care products" include skin creams, moisturizers, lotions, and body washes.

Skin Care Product

The skin care product described herein includes a skin care composition containing one or more skin care actives, one of which is Pal-KTTKS (SEQ ID NO: 1), and an applicator that includes a magnetic array tailored to enhance delivery of the Pal-KTTKS (SEQ ID NO: 1) into skin. The skin care composition and applicator may be packaged and sold together as a single product offering and/or they may be packaged separately to be sold individually. In some instances, the skin care composition and the applicator may be packaged in separate packages (e.g., in individual primary packages), which are then joined to one another or placed in a single secondary package. It may be desirable to include indicia on the applicator, the skin care composition and/or their respective package(s), which indicate that the magnetic properties of the array are tailored for use with the skin care composition, for example, to enhance penetration of one or more skin care actives. Indicia suitable for such use are not particularly limited and may include, for example, words, letters, numbers, shapes, colors, pictures and diagrams, which communicate to a consumer that the magnetic array is intended for use with the corresponding cosmetic composition. In some instances, the indicia may provide a non-verbal communication to a user that the magnetic array enhances penetration of Pal-KTTKS (SEQ ID NO: 1).

Applicator

The cosmetic skin care product described herein includes a suitable applicator for either applying a skin care composition to a target portion of skin or placing above and/or contacting a target portion of skin to which a skin care composition has already been applied. The form of the applicator may vary according to the intended target area of application on skin. For example, if the skin care composition is a whole body cream, then the applicator may be sized and/or shaped to apply the composition to larger surfaces and/or body parts (e.g., the legs, arms, abdomen and/or back). In some instances, the skin care composition may be intended for use in smaller areas such as the face (e.g., cheeks, forehead, chin, nose, and peri-orbital regions). In such cases, the applicator may be correspondingly shaped and sized to use with smaller surface areas.

A magnetic array for incorporation into the present applicators may be configured to provide a skin contacting surface of the applicator (i.e., the magnetic array is disposed on the applicator such that it is brought into contact with a target skin surface when the applicator is used as intended). Thus, it is important for the magnetic material to be safe for topical use on skin, especially when used with a topical skin care composition. It may be desirable to select a magnetic material that provides a pleasant feel contacted with skin. For example, the magnetic array may be embedded in the applicator such that the applicator and the magnetic array are a unitary device that provides a smooth, comfortable surface when contacted with skin.

In some instances, the applicator may include an optional cover placed over at least a portion of the magnetic array and/or skin contacting surface, such that the cover becomes the skin contacting surface of the applicator. The cover may be permanently joined to the applicator, or the cover may be removable, detachable and/or replaceable. It may be desirable for the cover to have a coefficient of friction that is less than that of the magnetic substrate of the magnetic array, which can provide a more desirable user experience when applying a skin care composition with the applicator. In some instances, the cover may have a dry coefficient of friction (i.e., a coefficient of friction measured without using a composition) that is between 10 and 50% less than the magnetic substrate (e.g., 15%, 20%, 25%, 30%, 35%, 40%, or even 45% less) according to the Friction Test described in Example 3 below. When used to apply a skin care composition, the cover may exhibit a coefficient of friction that is up to 10 times less than the magnetic array (e.g., between 2× and 10× less, 3× and 7× or even between 4× and 6× less).

The optional cover, when included, may be formed from a material that provides a skin contacting surface with better cooling properties than the magnetic substrate. For example, the cover may be formed of a material that has a high thermal conductivity of, for example, at least 50 W/mK, 100 W/mK or 200 W/mK. Providing a cover with high thermal conductivity feels cool when contacted with skin. Because the thickness of the cover affects the distance that the magnetic flux density of the magnetic array extends, especially when formed from a non-magnetic material, it is important to ensure that the thickness of the cover does not undesirably inhibit the strength of the applied magnetic field. Suitable cover thicknesses are between 0.1 mm and 5 mm (e.g., between 0.2 and 4 mm, 0.5 and 3 mm, or even between 1 and 2 mm), for non-magnetic materials.

FIGS. 1A, 1B and 1C and 1D show non-limiting examples of applicators 100, 200, 300 and 400, respectively, for use in the present skin care products. The applicator 100 shown in FIG. 1A has a substantially cylindrical base 102 with a skin contact surface 104 extending across the base. A handle 106 extends from the base in a direction substantially perpendicular to the skin contact surface. A magnetic array is disposed inside the base (not shown), adjacent to and in parallel with the skin contact surface so that, in use, the magnetic array will be substantially parallel to any surface on which the applicator is used.

Figure 1B:
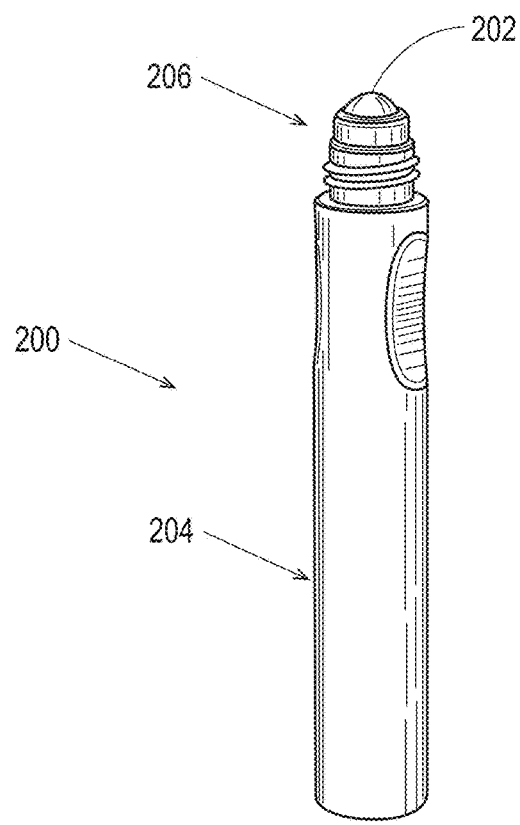

The applicator 200 shown in FIG. 1B has a rounded tip 202 that may be suitable for use around the eye. The rounded tip 202 may be integrally formed with a handle 204, or it may be formed as a ball held within a socket 206 at the end of the handle 204. A magnetic array (not shown), formed of a flexible substrate is disposed inside the rounded tip 202, such that as the tip 202 is rolled over a surface of skin, the magnetic array will be substantially parallel to the surface of skin. Thus, the tip 202 functions as a cover for the magnetic array disposed within the tip 202.

Figure 1C:
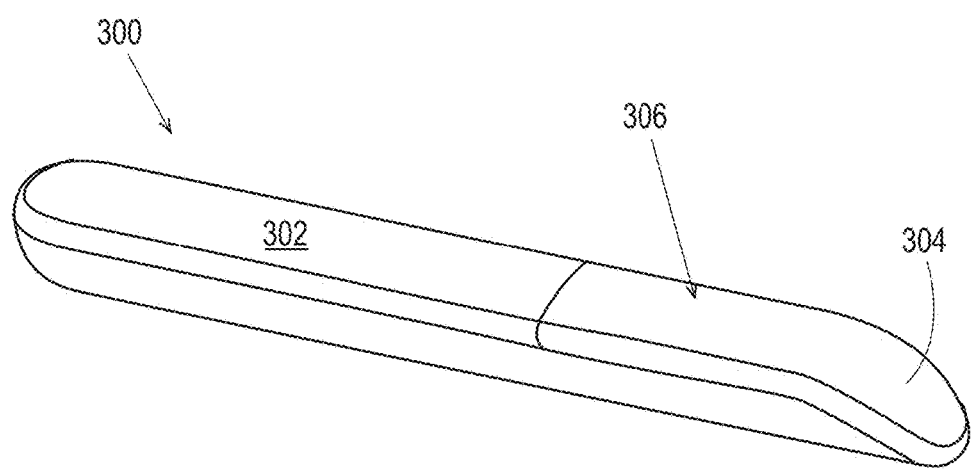

The applicator 300 shown in FIG. 1C has an elongate handle 302 with a skin contacting tip 304 disposed on a skin facing side 306 of the applicator 300. A magnetic array (not shown) can be disposed inside the applicator 300, adjacent to and in parallel with the skin contact tip, such that the magnetic array will be substantially parallel to any surface on which the applicator 300 is used.

Figure 1D:
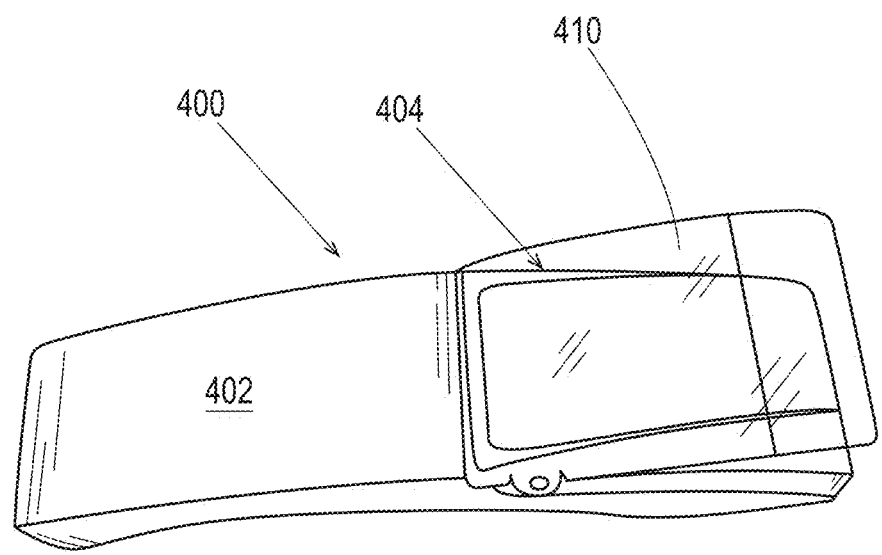

The applicator 400 shown in FIG. 1D includes a removable cover 410 disposed at one end of the applicator 400 and a handle 402 disposed at the other end of the applicator 400. The cover 410 is joined to the skin facing side 404 of the applicator 400 and forms a skin contacting surface of the applicator 400, when used as intended. The cover 410 may be removed and/or replaced, as desired. In some instances, the cover 410 may be removed and reattached, for example, to facilitate cleaning the cover 410 and/or applicator 400. In some instances, the cover 410 may be disposable. For example, the cover 410 may be removed and discarded after one or more uses, but typically less than ten uses, and replaced with a different cover. The cover 410 may be joined to the applicator 400 by any suitable means known in the art.

The applicators herein may be used to directly apply a skin care composition, or used to enhance penetration of skin care actives within a skin care composition after application of the skin care composition by some other means, for example, by finger application. For example, the applicator may be designed for movement across the skin's surface—either through manual operation or mechanical means (e.g., a vibrating device) or held in position stationary above a target area of skin to which a skin care composition has been applied. A vibrating device may include any mechanism, electrical or mechanical, adapted for reciprocal and/or rotational movement of the magnetic material. For example, the magnetic material may be associated with a drive mechanism that is capable of reciprocal movement.

Alternatively, the applicator may be made in the form of, for example, a leave-on patch, in which case the applicator may be formed of a woven, flexible fabric. The patch may be formed with an adhesive section such that it can be adhered to a skin's surface following application of the skin care composition or the skin care composition may be contained within the patch.

Magnetic Array

The present applicator includes a magnetic array specifically tailored to provide improved penetration of Pal-KTTKS (SEQ ID NO: 1). The magnetic array described herein uses selectively magnetized permanent magnets to generate a magnetic field. The magnets may be formed of any suitable ferromagnetic substrates, including, but not limited to: iron or an iron containing material (e.g., a ferrite such as barium ferrite, magnetite, or mild steel), a cobalt material, a strontium material, a barium material, a nickel material, alloys and oxides of these, combinations thereof and the like. In some instances, the magnetic array substrate may include a metalloid component such as boron, carbon, silicon, phosphorous or aluminum. Rare earth material such as neodymium or samarium may also be used.

Figures 2A, 2B:
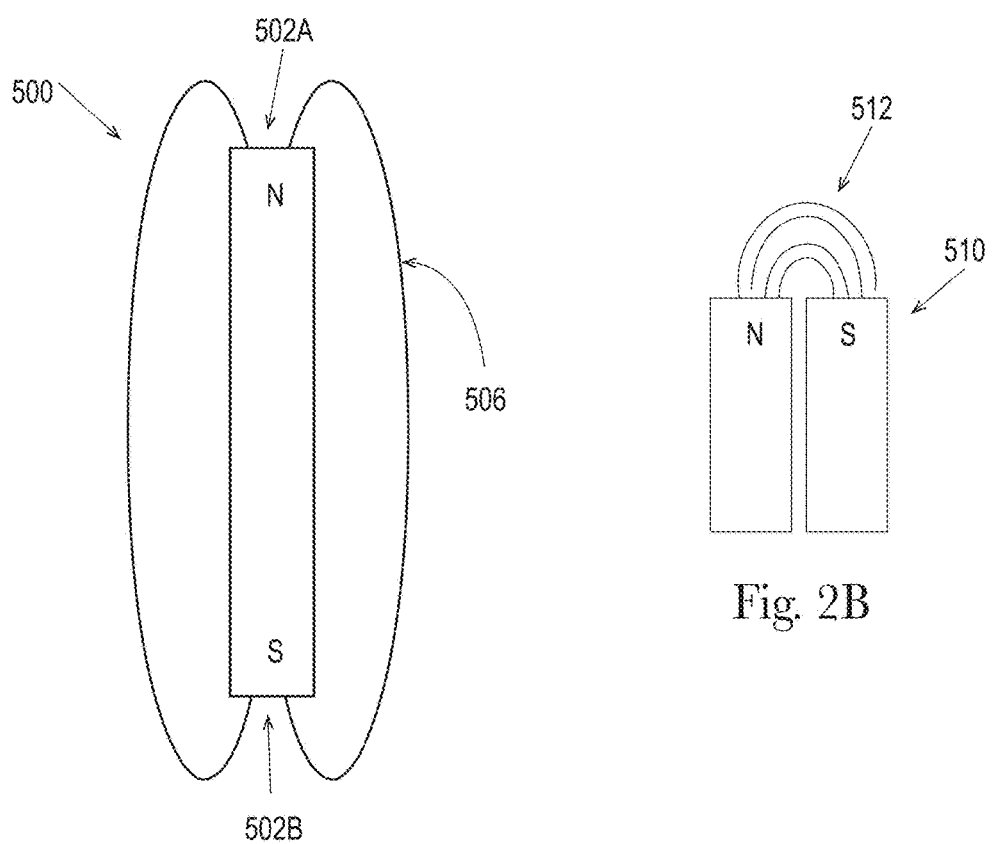
FIG. 2A shows schematically a typical bar magnet having a north and south pole.
FIG. 2B shows schematically a dipolar pair of magnets.

In a conventional bar magnet 500 such as the one illustrated in FIG. 2A, the magnetic field 506 extends between opposite ends 502A and 502B of the magnet 500. In contrast with a conventional bar magnet, the magnetic array(s) described herein are formed of one or more dipole pairs of magnetic elements where magnetic poles of opposite polarity (N and S) are positioned adjacent one another, and the magnetic field extends between adjacent opposing poles. For purposes of visualization, a dipole pair may be thought of as a conventional rod magnet that is cleaved at its center and the resulting sections brought together in a north-south (NS), side-by-side configuration.

Figure 2C:
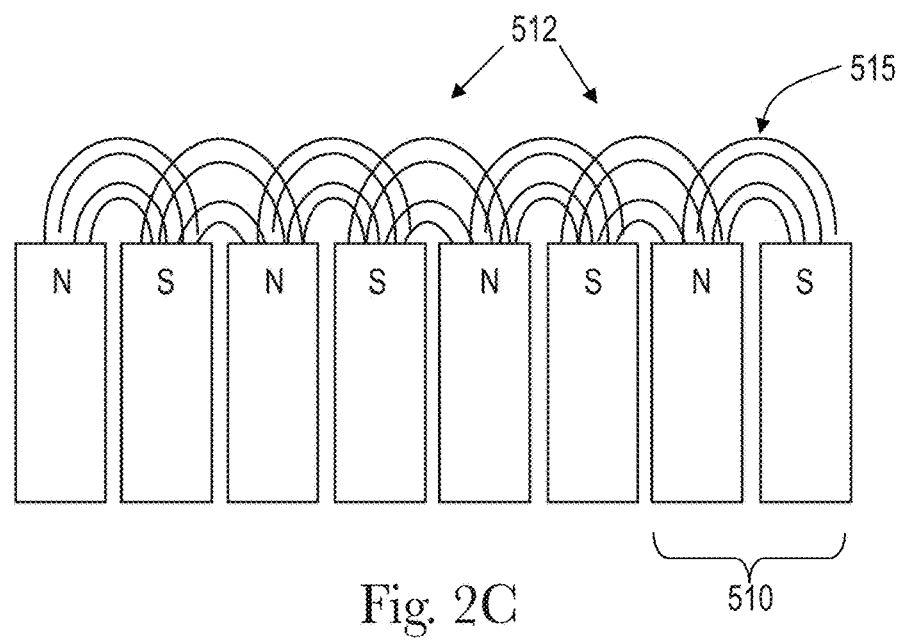
FIGS. 2C and 2D show schematically different arrangements of dipolar pairs in a magnetic array.
Figure 2D:
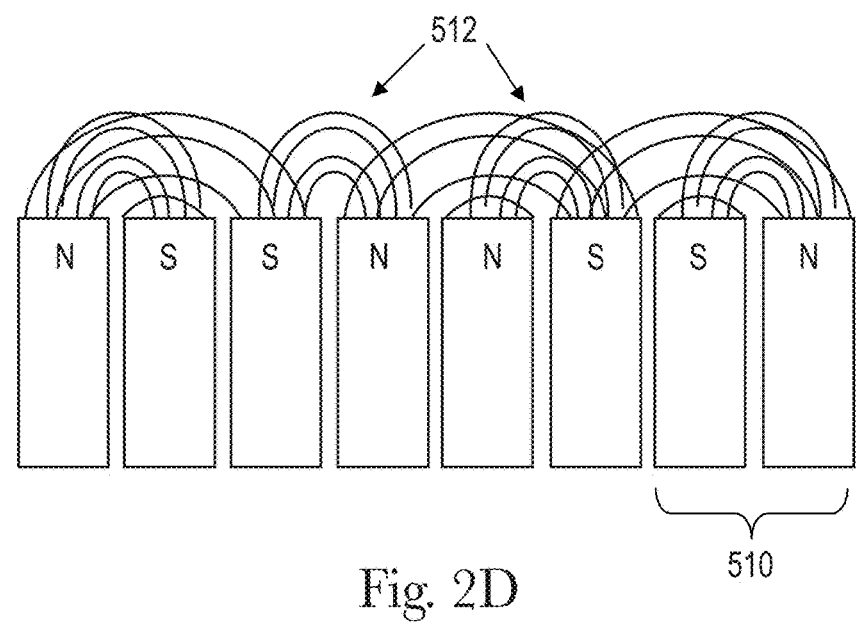

FIGS. 2B, 2C and 2D illustrate examples of magnetic arrays 510. Each of the magnetic arrays in FIGS. 2B, 2C and 2D include one or more dipole pairs 510. Magnetic fields 512 corresponding to the magnetic interaction of the dipole pairs 510 are represented by curved lines. FIG. 2B illustrates a magnetic array with one dipole pair 510 with a single corresponding magnetic field 512, whereas FIGS. 2C and 2D show multiple dipole pairs 510 arranged in series with multiple corresponding magnetic fields 512. When a magnetic array includes multiple dipole pairs 510, such as illustrated in FIGS. 2C and 2D, each dipole pair 510 can be in the same or a different orientation as that of the neighboring dipole pair 510 (e.g., [NS][NS][NS] or [NS][SN][NS]). In use, the magnetic fields 512 generated by the dipole pairs 510 will induce a magnetic field in a diamagnetic material. The induced magnetic field of the diamagnetic material interacts repulsively with the applied magnetic field 512 of the dipole pairs 510 regardless of the direction of the applied field 512 (i.e., north or south). The magnitude of the repulsive force between the magnetic field 512 of the dipole pairs 510 and the diamagnetic material is determined by the magnetic flux density of the corresponding dipole pair 510 and the diamagnetic susceptibility of the diamagnetic material, in this case the skin care active. Magnetic susceptibility is a dimensionless proportionality constant that indicates the degree of magnetization of a material in response to an applied magnetic field. A negative magnetic susceptibility generally indicates diamagnetism and is referred to herein as diamagnetic susceptibility. Magnetic flux density is generally greatest at the mid-point 515 between the corresponding poles, and thus the strength of the magnetic field 512 will typically vary across the magnetic array depending on how the array is configured.

Figure 3A:
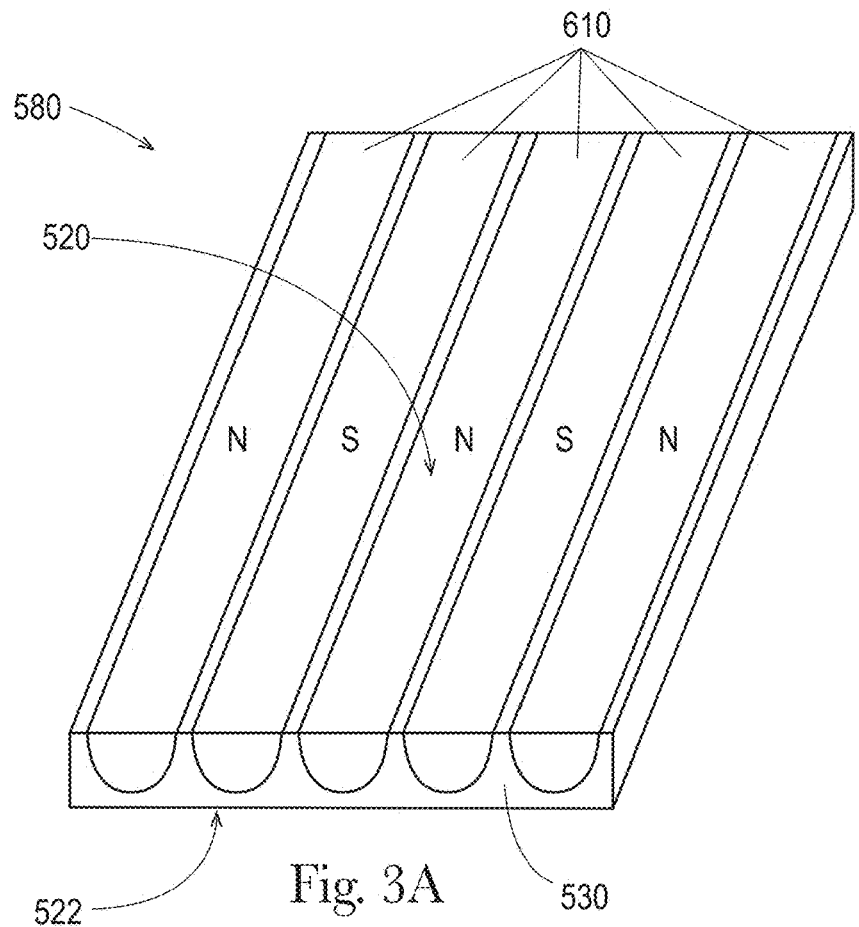
FIGS. 3A to 3E illustrate schematically the magnetization and corresponding magnetic field generated in a magnetic array.
Figure 3B:
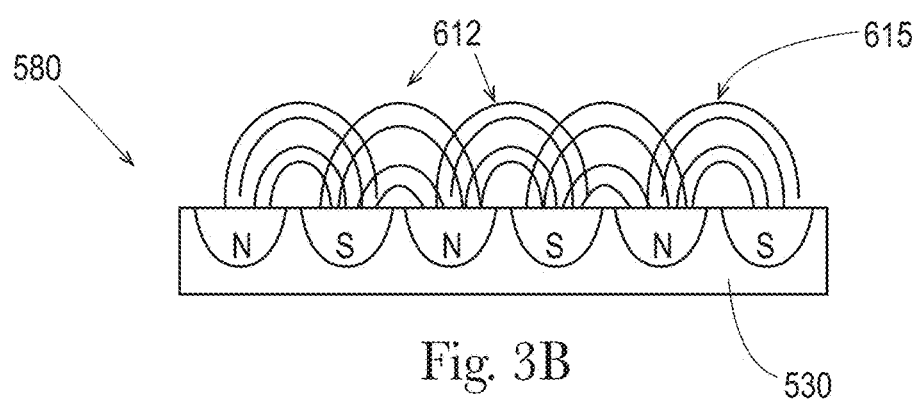

In practice, the substrate 580 used to form a magnetic array for use herein is typically not magnetized evenly throughout. As shown in FIG. 3A, each pole 610 extends from an upper skin facing side 520 of the substrate 580 towards an opposing underside 522 (i.e., through the thickness of the substrate 580). A magnetic return 530 is provided between each adjacent pole 610 and at the second side 522 of the substrate 580. The magnetic return 530 is an unmagnetized area used to integrate the magnetic fields 612 generated by each pole 610 on that side of the substrate 580 and reduce or eliminate the magnetic flux on the second side 522 of the substrate 580, instead diverting it towards the skin facing side 520. The resultant magnetic field 612 extends outward from the first side 520 of the substrate 580, in a direction substantially perpendicular to the surface of the substrate 580, and is strongest at the mid-point 615 between adjacent opposing poles 610.

Figure 3C:
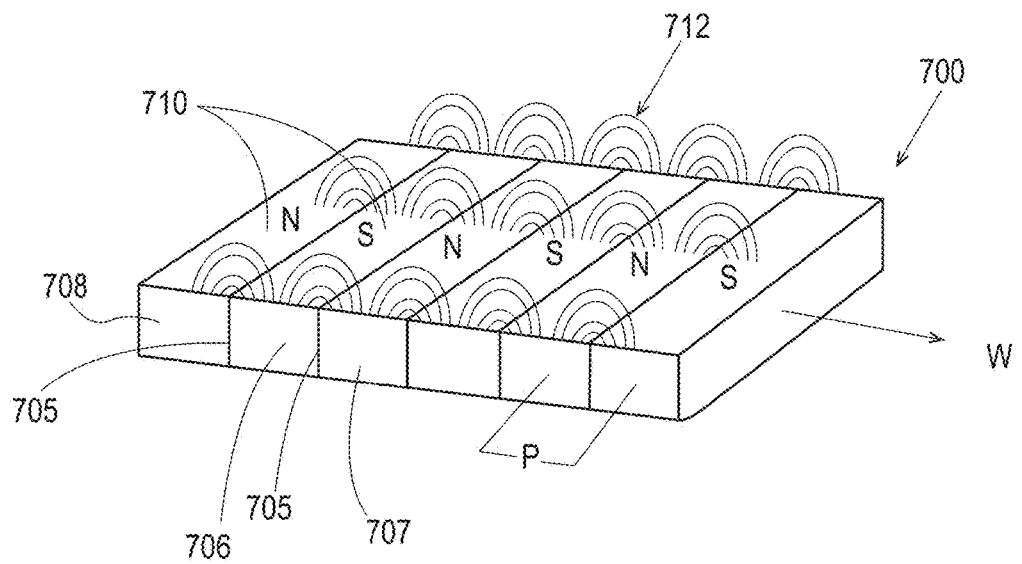

The magnetic array herein may be formed as a uni-directional array or a multi-directional array. FIG. 3C illustrates an example of a uni-directional array 700. The uni-directional array 700 has north (N) and south (S) poles 710 aligned in parallel to one another in a single layer. Adjacent poles 710 are separated from one another by a pole center-to-center distance P, which defines the pitch of the magnetic array 700.

Figure 3D:
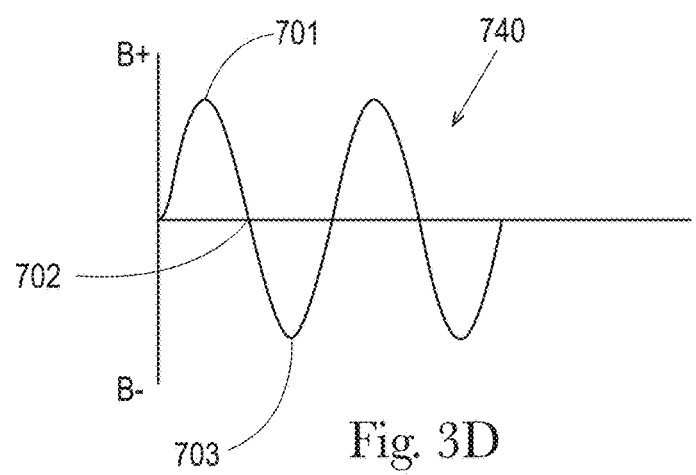

FIG. 3D illustrates a portion of the magnetic field 712 generated by the magnetic array 700 of FIG. 3C in a direction W that is perpendicular to the alignment of the poles 710. The waveform 740 illustrated in FIG. 3D shows the magnitude of the magnetic field 712 varying regularly between +B and −B in a sinusoidal pattern, which corresponds to the difference in polarity (i.e., direction) of the magnetic field 712. The peaks 701 and troughs 703 of the waveform 740 correspond to the mid-points 705 between adjacent poles 710, and the inflections points 702 of the waveform 740 correspond to the centers of the poles 710. In other words, a first maximum magnetic flux density is represented by peak 701, which occurs at a mid-point 705 between a first north pole 708 and an adjacent south pole 706, a minimum magnetic flux density represented by inflection point 702 occurs in the center of the south pole 706, and a second maximum magnetic flux density represented by trough 703 occurs at the mid-point 705 between the south pole 706 and a second north pole 707 adjacent the south pole 706.

The amplitude of the waveform 740 is determined by the choice of magnetic substrate, the thickness or depth of substrate that is magnetized and the distance from the center of a pole 710 to the edge of the pole 710. As the depth of magnetized area of a given substrate material increases, the maximum amplitude of the waveform 740 increases.

The frequency of the waveform 740 is determined by the pitch P of the array 700. A higher pitch P means that there are fewer magnetic flux density "maximums" per area of substrate, and thus a lower overall magnetic field strength for the array 700. However, a lower pitch P may result in respective poles 710 being packed too closely to one another for any single pole 710 to reach its maximum potential magnetic flux density.

Figure 3E:
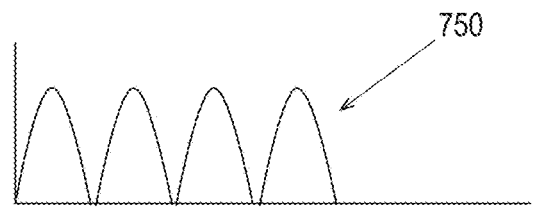

FIG. 3E is an illustration of a waveform 750 representing the repulsive force that would be experienced by a diamagnetic material exposed to the magnetic field 712 in FIG. 3D. As shown by the waveform 750, the induced magnetic field of a diamagnetic material is independent of the direction of the applied magnetic field 712, and thus the change in the magnitude of the repulsive force corresponds to the change in magnitude of the applied magnetic field 712.

In some instances, the magnetic array herein may be formed as a multi-directional array (e.g., bi-directional array), whereby multiple layers of parallel poles, which may be configured to play different roles, are juxtaposed at an angle relative to one another to provide multiple magnetic fields that constructively or destructively interfere with one another. For example, a first layer of poles may determine the maximum magnetic field strength, while a second set of poles smooths out the overall profile of the magnetic field, thereby reducing instances of minimum magnetic flux density and ineffectual magnetic field strength. Generally, in a multi-directional array, the magnetic flux density at any one point in the magnetic array will be determined by the combined magnetic flux density of poles of the different layers at that point. In some cases, this will lead to constructive interference where the resultant magnetic flux density at a point is greater than the magnetic flux density at that point for each individual layer. In other cases, the combination may lead to destructive interference where the resultant magnetic flux density at a point is less (sometimes zero) than the magnetic flux density at that point for each individual layer.

Figure 4A:
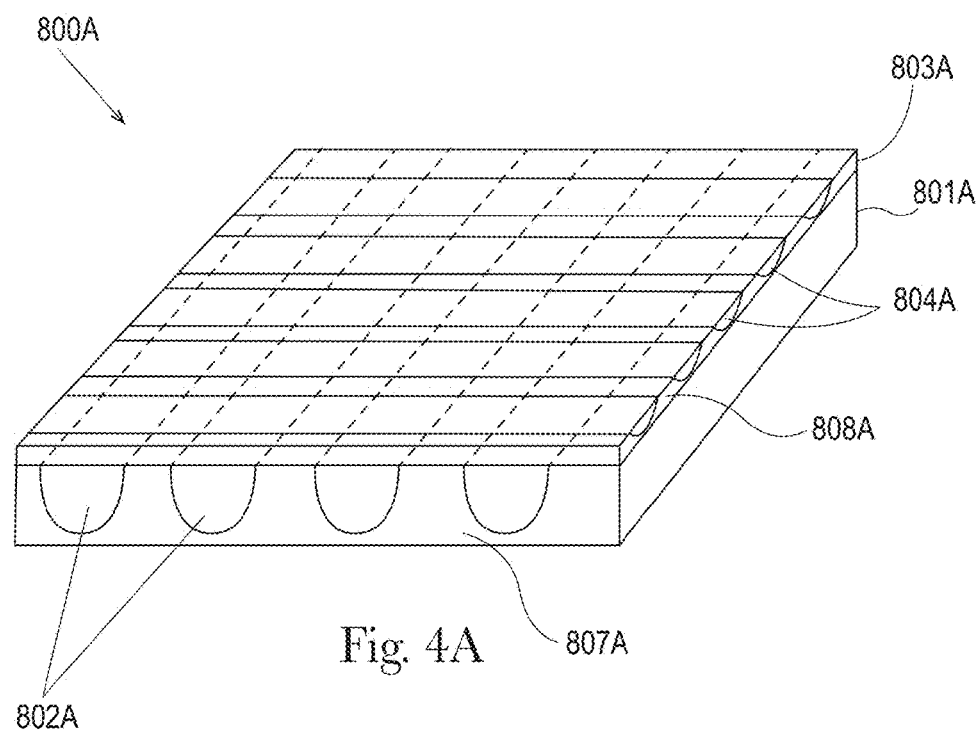
FIGS. 4A and 4B illustrate schematically different ways of constructing a bi-directional magnetic array.

FIG. 4A illustrates an example of a bi-directional array 800A, wherein the first and second layers of poles 802A and 804A, respectively, are formed in two separate magnetic substrates 801A and 803A, which are juxtaposed at an angle offset from one another. The magnetic returns 807A and 808A of the substrates 801A and 803A are positioned to face in the same direction such that the magnetic field generated by both layers of poles 802A and 804A extends away from the magnetic array 800A in the same direction. The layers of poles 802A and 804A may be identical to one another (for example, having the same pitch between adjacent poles and the same maximum field strength), or the two layers 802A and 804A may vary in their specific parameters. Where the parameters of the two layers 802A and 804A vary, it is preferable for the layer that is proximate the target diamagnetic material (in FIG. 4A, the second layer 804A) be formed of a thinner substrate than the distal layer (in FIG. 4A, the first layer 802A), otherwise the induced magnetic field of the diamagnetic material will be primarily based on the magnetic field strength of the proximal layer.

Figure 4B:
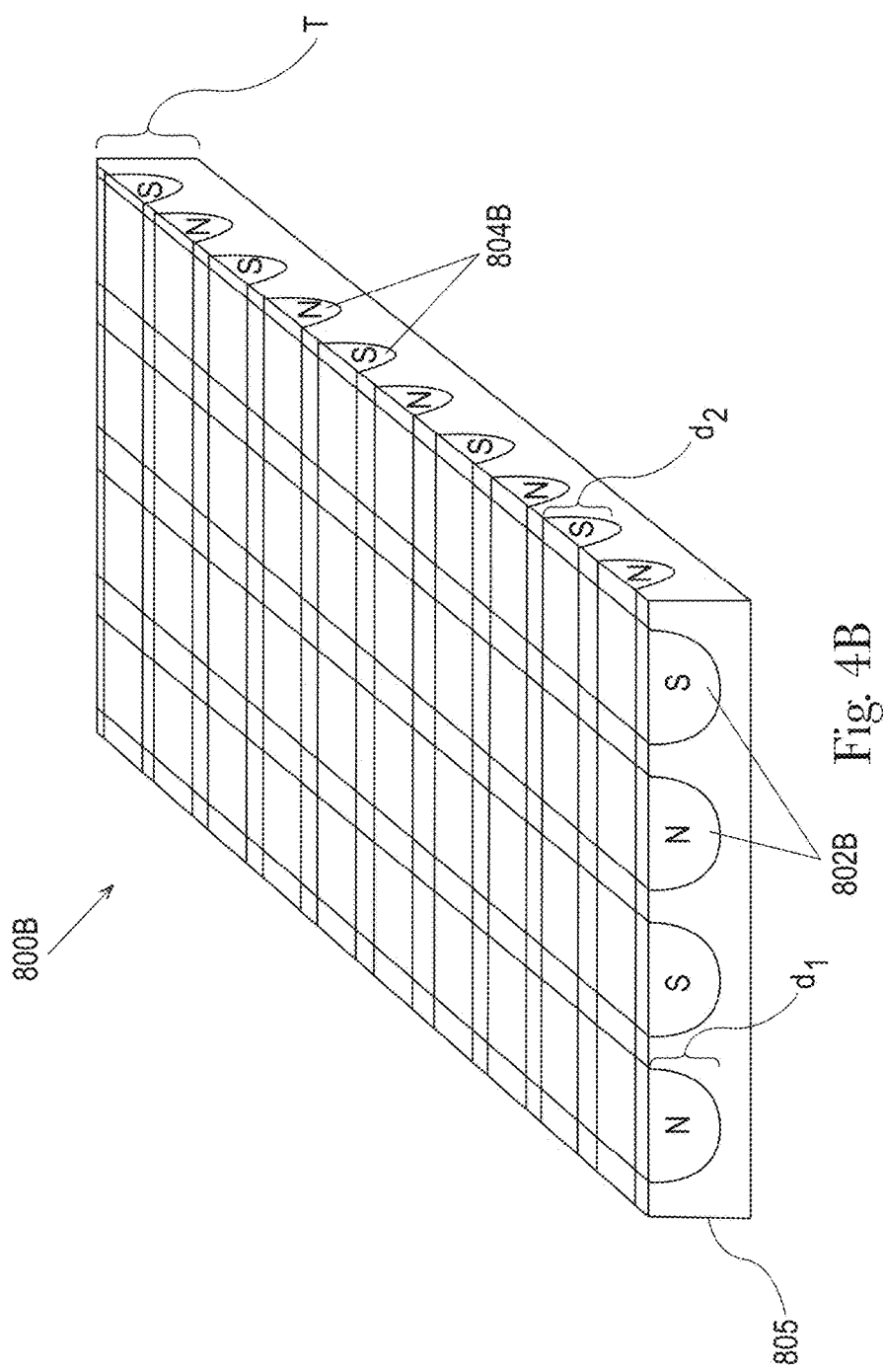

FIG. 4B illustrates an example in which the first layer of poles 802B and the second layer of poles 804B are formed in the same magnetic substrate 805. The configuration shown in FIG. 4B may be provided by magnetizing the substrate 805 in one direction to form a first layer of parallel aligned north and south poles 802B, and then remagnetizing the substrate 805 in a different direction to form a second layer 804B of parallel aligned north and south poles to effectively form a woven pattern of poles. In this embodiment, the depth of poles d2 in the second layer 604 is equal to or less than the depth d1 of poles in the first layer 802B. The depth d1 of the first layer 802B of poles is typically determined by the thickness T of the magnetic substrate 805.

Figure 4C:
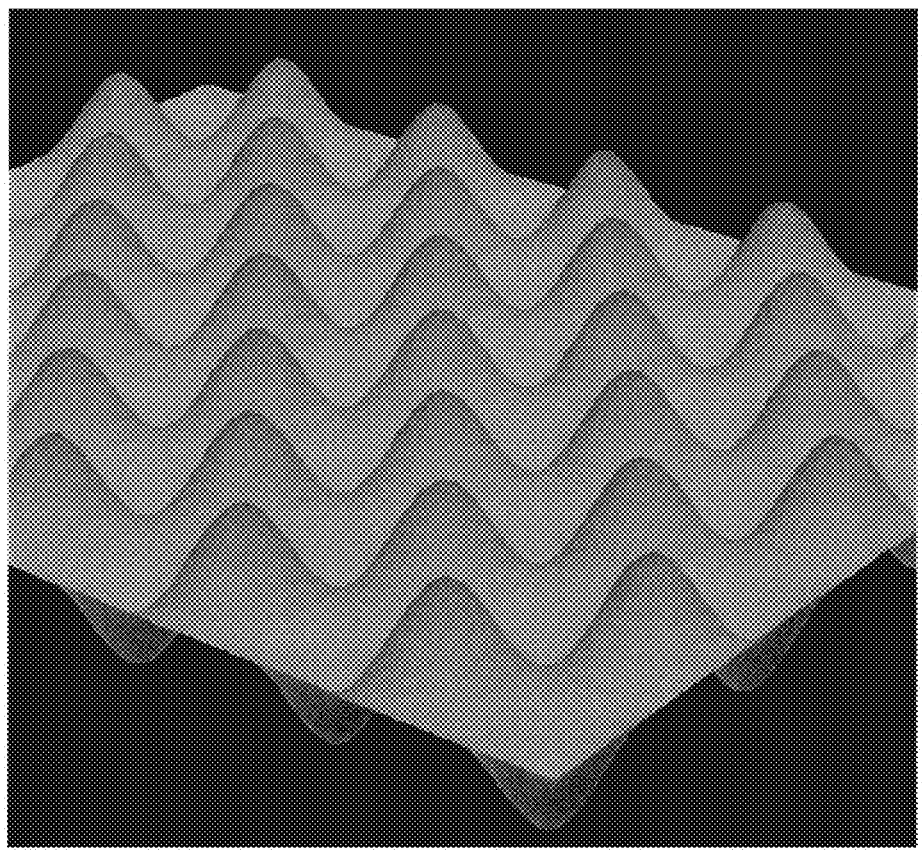
FIG. 4C shows schematically a representation of the magnetic field generated by a bi-directional array.

FIG. 4C illustrates a waveform representing the three-dimensional magnetic field of a bidirectional magnetic array. The induced magnetic field of a diamagnetic material is independent of the direction of the magnetic field, and thus all areas of positive and negative magnetic field strength will appear as a repulsive force to a diamagnetic material.

The combined overall magnetic field strength of a magnetic array can be measured after completion of the magnetization process using any known Gaussmeter. For bi-directional magnetic arrays made of two separate substrates, the overall magnetic field strength can be measured first for the respective layers and subsequently for the combined bi-directional magnetic array. In a bi-directional magnetic array, the overall magnetic field strength will approximately equate to the sum of the field strength of the individual layers.

Dipolar pairs of the magnetic substrate may be separated from adjacent dipolar pairs by a magnetically insulating material (i.e., a material with a relatively low magnetic permeability). In some instances, the magnetic elements may be arranged as individual segments or sections of magnetized ferromagnetic materials. Additionally or alternatively, the magnetic elements may be disposed in or on a solid or semi-solid substrate in which the required magnetic pattern is impressed upon the ferromagnetic particles or elements. The magnetic elements may be rigid elements within the applicator itself or disposed on a suitable substrate and joined to the applicator, for example, with an adhesive. In some instances, it may be desirable to embed the magnetic elements in a flexible matrix such as rubber or silicone and join the resultant array to a skin facing surface of the applicator.

In a particularly suitable example of a skin care product, a magnetic array is paired with a skin care composition that includes Pal-KTTKS (SEQ ID NO: 1). Pal-KTTKS (SEQ ID NO: 1) has a diamagnetic susceptibility of approximately −519. Magnetic arrays suitable for enhancing the penetration of Pal-KTTKS (SEQ ID NO: 1) include uni-directional and/or bi-directional arrays that exhibit enhanced penetration of cosmetic actives with a diamagnetic susceptibility of between about −400 and −600. A suitable example of a uni-directional magnetic array for enhancing the penetration of Pal-KTTKS (SEQ ID NO: 1) into skin is a magnetic array formed from a strontium ferrite powder impregnated in a polyvinyl chloride PVC base. In this example, the magnetic array may have a thickness of between 0.9 and 1.3 mm (e.g., 1.0, 1.1 or 1.2 mm); a pitch of between 1.7 and 2.5 mm (e.g., 1.8, 1.9, 2.0, 2.1, 2.2, 2.3 or 2.4 mm); and an overall field strength of from 24.0 to 36.0 mT (e.g., about 24.5, 25, 25.5, 26, 26.5, 27, 27.5, 28, 28.5, 29, 29.5, 30, 30.5, 31, 31.5, 32, 32.5, 33, 33.5, 34, 34.5, or even about 35 mT). In a particularly suitable example of a uni-directional magnetic array, the magnetic array has an overall magnetic field strength of approximately 27 mT, a thickness of 1.1 mm and a pitch of about 2.1 mm (e.g., 12 poles per 25.4 mm).

An example of a suitable bi-directional array for enhancing the penetration of Pal-KTTKS (SEQ ID NO: 1) into skin may have a first layer thickness of between about 0.3 and 0.9 mm (e.g., 0.4, 0.5, 0.6, 0.7 or even 0.8 mm) and a first layer pitch of between 1.7 and 2.5 mm or about 12 poles per 25.4 mm (e.g., a pitch of 1.8, 1.9, 2.0, 2.1, 2.2, 2.3 or 2.4 mm), leading to a first layer magnetic field strength of between 20 mT and 26 mT (e.g., 21, 22, 23, 24 or even 25 mT), especially about 23.2 mT. The bi-directional array in this example may have second layer thickness of between 0.05 mm and 0.5 mm (e.g., 0.1, 0.15, 0.2, 0.25, 0.3, or even 0.4 mm) and a second layer pitch of about 0.8 mm to about 1.3 mm or 25 poles per 25.4 mm (e.g., a pitch of between 0.9 and 1.2 mm or between 1.0 and 1.1 mm), leading to a second layer field strength of between 1 mT and 24 mT (e.g., 2, 3, 4, 5, 6, 7, 8, 9, 10, 11, 12, 13, 14, 15, 16, 17, 18, 19, 20, 21, 22, or 23 mT). The overall magnetic field strength of the bi-directional array may be between 14 mT and 30 mT (e.g., 15, 16, 17, 18, 19, 20, 21, 22, 23, 24, 25, 26, 27, 28 or 29 mT). The bi-directional array may have an overall magnetic field strength of between about 19.0 and about 25.0 mT (e.g., 20, 21, 22, 23, or even 24 mT). Typically, in a bi-directional array, the magnetic field strength of the second layer will be less than or equal to the magnetic field strength of the first layer, and/or the second layer pitch will be less than or equal to the first layer pitch. The first and second layers of the bi-directional array in this example may be formed from uni-directional arrays that are angularly offset by between 1 and 179 degrees (e.g., between 45 and 135 degrees, between 60 and 120 degrees, or even about 90 degrees).

Skin Care Composition

The skin care composition herein can help improve the appearance of visible and/or tactile discontinuities in mammalian skin, including fine lines, wrinkles, enlarged pores, roughness, dryness, and other skin texture discontinuities, e.g., reduces or effaces the visibility of fine lines, wrinkles, and other forms of uneven or rough surface texture associated with aged or photo-damaged skin. The skin care compositions in the present skin care product may be applied to mammalian keratinous tissue, in particular to human skin. The skin care composition may take various forms such as, for example, solutions, suspensions, lotions, creams, gels, toners, sticks, pencils, sprays, aerosols, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks, cosmetics such as foundations, eye liners, eye shadows, and the like.

The present skin care compositions contain a safe and effective amount of Pal-KTTKS (SEQ ID NO: 1), for example, Matrixyl® or Promatrixyl® brand Pal-KTTKS (SEQ ID NO: 1) (100 ppm Pal-KTTKS (SEQ ID NO: 1)) available from Sederma, France. The Pal-KTTKS (SEQ ID NO: 1) may be included in the present skin care composition at an amount of from $1\times10^{-6}\%$ to 10% by weight of the composition (e.g., $1\times10^{-6}\%$ to 0.1%, even from $1\times10^{-5}\%$ to 0.01%). In embodiments wherein Matrixyl® or Promatrixyl® is used, the resulting composition preferably contains from 0.01% to 50%, by weight of the resulting composition, of Matrixyl® or Promatrixyl® (e.g., from 0.05% to 20%, or from 0.1% to 10%). The present skin care compositions may include additional optional ingredients known for safe use in skin care compositions (e.g., emollients, humectants, vitamins; peptides; and sugar amines, sunscreen actives (or sunscreen agents), ultraviolet light absorbers, colorants, surfactants, film-forming compositions, and rheology modifiers). Some non-limiting examples of optional ingredients for use in the present compositions are disclosed in U.S. Publication No. US2008/0206373, filed by Millikin, et al., on Feb. 28, 2008.

Methods of Use

The skin care product disclosed herein may be used to apply a skin care composition to one or more skin surfaces as part of a user's daily routine. Additionally or alternatively, the cosmetic compositions herein may be used on an "as needed" basis. For example, the cosmetic composition may be applied to a facial skin care surface in need of treatment. The facial skin surface may include one or more of the cheek, forehead, and peri-orbital areas of the face. In some examples, one or more of these skin surfaces may be identified as needing treatment when signs of skin aging are observed on the target skin surface. In these instances, the present composition may be applied to the target skin surface. For example, the cosmetic composition can also be applied to the facial skin surface at least once per day, twice per day, or three times per day for a period of 7, 14, 21, or 28 days or more. In another example, the cosmetic composition may be applied to a different skin surface or applied to facial skin and one or more different skin surfaces.

Example 1—Pal-KTTKS (SEQ ID NO: 1) Ex Vivo Skin Penetration Study

An ex vivo skin penetration study was conducted to compare the ability of different magnetic arrays to enhance penetration of Pal-KTTKS (SEQ ID NO: 1) into the epidermis of human skin. The dermis and epidermis of human skin samples obtained from donors aged 60-65 years were heat separated and the dermis discarded. 20 μL of a Pal-KTTKS (SEQ ID NO: 1) containing composition (400 μg/ml in 50:50 PG:PB at pH 4) was placed on human epidermis in Franz cell. Different magnetic arrays were positioned approximately 1.0 mm above the epidermis samples and moved over the samples at the speed a user might move a cosmetic applicator when applying a skin care product (e.g., about 20-25 cm/sec). Samples were taken and measured at 0, 1, 2, 4, 6, 8, 24 hours. Of the arrays tested, two particular arrays, which are set forth in Table 1 below, demonstrated the best penetration enhancement of Pal-KTTKS (SEQ ID NO: 1). For the bi-directional arrays herein, the "1st layer" refers to the layer closest to the skin-contacting surface of the applicator, and the "$2^{nd}$ layer" refers to the layer disposed on the side of the $1^{st}$ layer opposite the side closest to the skin-contacting surface.

Pal-KTTKS (SEQ ID NO: 1) with an applicator comprising a magnetic array. The study compared the penetration of the Pal-KTTKS (SEQ ID NO: 1) in combination with a variety of magnetic arrays (active application) to the penetration of Pal-KTTKS (SEQ ID NO: 1) applied with a finger (passive application). Penetration of Pal-KTTKS (SEQ ID NO: 1) in this example is determined according to the Tape Stripping method. In this example, the level of Pal-KTTKS (SEQ ID NO: 1) present in the extract from each tape strip was measured using HPLC and the results normalized to the protein level measured on the tape strip. While passive delivery is accomplished using a finger, it is to be appreciated that passive delivery may also be accomplished using an applicator or other device that does not include a magnetic array tailored to enhance penetration of Pal-KTTKS (SEQ ID NO: 1).

Tape Stripping Method

This method provides a suitable means of measuring the amount of skin care active present in skin, and comparing active versus passive application of the skin care active. Two identical rectangular areas of 15 cm$^2$ are marked on the volar forearms of volunteers. A measured dose (approximately 30 mg) of the Pal-KTTKS (SEQ ID NO: 1) formulation is applied to the delineated areas using a screw actuated syringe. Active application is carried out on one of the delineated areas using the three-quarter profile of a purpose made applicator (e.g., an applicator presenting one of the magnetic arrays set forth in Table 2). Passive application is accomplished on the other delineated area using the tip of a finger in a sweeping motion identical to that of the active application. The formulation is spread evenly across the entire delineated region using a sweeping motion with a fixed speed of approximately 23 cm/s to mimic typical. The application period is 30 seconds during which time visual inspection is used to ensure even distribution and absorption of the formulation by skin. The application area is then left uncovered for a further 30 minutes to ensure complete absorption. Tape strip samples may be collected and/or analyzed immediately after the complete absorption is ensured or after a waiting period (e.g., after multiple applications of the formulation over multiple hours or days).

The tape stripping procedure is carried out using 10 commercial pre-cut 22.1 mm tape stripping adhesive discs (e.g., D-SQUAME brand tape strips, available from Cuderm Corporation, or equivalent) with an adhesive area of 3.8 cm$^2$. The 10 tape strips are applied sequentially to the same sampling site, which ideally enables each tape strip to obtain a sample from deeper within the stratum corneum than the tape strip that preceded it. A 22.1 mm diameter circular region is marked at the center of the application area. A tape

TABLE 1

| | Array | Thickness (mm) | Pitch (mm) | Poles per 25.4 cm | Magnetic Field Strength (mT) | Angle offset |
|---|---|---|---|---|---|---|
| 1 | Uni-directional | 1.1 | 2.13 | 12 | 27 | n/a |
| 2 | Bi-directional | 1st layer: 0.6<br>$2^{nd}$ layer: 0.2 | 1st layer: 2.13<br>$2^{nd}$ layer: 1.06 | 1st layer: 12<br>$2^{nd}$ layer: 25 | 1st layer: 27<br>$2^{nd}$ layer: ~4<br>Overall: 21 | 90° |

Example 2—Pal-KTTKS (SEQ ID NO: 1) In Vivo Skin Penetration Study #1

An in vivo skin penetration study was conducted to establish the effect of using a skin care product of the present invention by applying a skin care composition comprising stripping adhesive disc is placed over the marked area and even pressure applied using, for example, a neoprene roller, rolled ten times over the adhesive disc. The adhesive disc is removed from the skin surface in a single pulling motion using manual tweezers. To ensure even removal of the skin sample, subsequent discs are removed in a "north, south, east and west" orientation, which is within the skill of the ordinary artisan. Each adhesive disc is non-destructively analyzed for protein content using a suitable instrument (e.g., SquameScan™ 850 instrument commercially available from Heiland Electronics Wetzlar, Germany, or equivalent). The adhesive disc is then immediately placed into a glass vial containing extraction solvent in preparation for subsequent analysis. Solvent extractions are conducted on each tape strip using conventional extraction methods, which are well known to those of ordinary skill in the art, and measuring the amount of Pal-KTTKS (SEQ ID NO: 1) present in the extract, for example, by high performance liquid chromatography ("HPLC") and/or mass spectrometry.

The procedure is repeated for the remaining nine strips. An additional strip is obtained from outside the area of application of the skin care formulation to serve as a blank sample. The amount of active is normalized to the amount of protein measured.

Delivery of the Pal-KTTKS (SEQ ID NO: 1) is said to be enhanced when a ratio of active to passive delivery, as determined according to the Tape Stripping method, is greater than 1. In other words, if active application of the skin care composition yields more Pal-KTTKS (SEQ ID NO: 1) as compared to the corresponding passive application, then delivery is said to be enhanced. The active and corresponding passive application values may be compared individually (e.g., single tape strip comparison) or as group of two or more values (e.g., the sum total and/or average values of tape strips 8, 9, and 10 for the active and passive applications may be compared to determine if penetration was enhanced). The tailored magnetic arrays herein enhance delivery of Pal-KTTKS (SEQ ID NO: 1). Enhanced delivery may be from 1.5× to 20× (2×, 2.5, 3×, 3.5×, 4×, 4.5×, 5×, 5.5×, 6×, 6.5×, 7×, 7.5×, 8×, 8.5×, 9×, 9.5× or even 10× or more).

Table 2 shows the magnetic arrays used in the tests described in more detail below. The magnetic arrays shown in Table 2 provide a variety of configurations to compare how different magnetic arrays enhance penetration of the Pal-KTTKS (SEQ ID NO: 1) in vivo. The magnetic arrays in Table 2 vary in thickness, pitch, and/or magnetic field strength. The two layers of magnetic arrays in the bi-directional arrays shown in Table 2 (i.e., arrays #8 and #9) are angularly offset by 90 degrees.

Table 3 shows the amount of Pal-KTTKS (SEQ ID NO: 1) (ng/strip normalized for protein content) measured on ten tape strip samples from a first test subject after active application of a Pal-KTTKS (SEQ ID NO: 1) formulation using several of the arrays in Table 2. The array number shown in Table 3 corresponds to the array of the same number in Table 2. Table 4 shows the average amounts (ng/strip) of Pal-KTTKS (SEQ ID NO: 1) measured on ten tape strip samples from a first test subject after passive application of the same Pal-KTTKS (SEQ ID NO: 1) formulation using a finger. The array number shown in Table 4 indicates which array in Table 3 the passive application is being compared to. Tape stripping and analysis of the resulting samples was conducted according to the Tape Stripping method, and commenced at the conclusion of four days and 8 applications of the Pal-KTTKS (SEQ ID NO: 1) formulation (2 applications per day). Array #4 was tested twice.

TABLE 3

Active Application

| strip | Array 1 | 2 | 3 | 4 | 4 | 5 | 6 | 8 | 9 |
|---|---|---|---|---|---|---|---|---|---|
| 1 | 56.96 | 46.92 | 61.09 | 35.01 | 45.77 | 33.38 | 59.87 | 39.68 | 73.27 |
| 2 | 49.66 | 53.18 | 40.67 | 46.41 | 21.58 | 23.71 | 54.00 | 37.11 | 57.70 |
| 3 | 46.77 | 29.37 | 43.64 | 58.65 | 35.26 | 26.85 | 36.23 | 24.63 | 60.39 |
| 4 | 41.88 | 66.20 | 22.16 | 53.42 | 25.62 | 28.25 | 41.38 | 21.71 | 59.04 |
| 5 | 38.78 | 53.17 | 28.93 | 43.64 | 28.78 | 23.41 | 34.55 | 23.23 | 51.72 |
| 6 | 30.80 | 36.55 | 35.18 | 50.02 | 41.63 | 30.99 | 27.18 | 22.53 | 44.43 |
| 7 | 34.10 | 51.40 | 34.45 | 61.19 | 47.01 | 29.47 | 27.17 | 21.41 | 35.56 |
| 8 | 23.34 | 41.22 | 44.32 | 48.91 | 24.72 | 38.99 | 55.02 | 24.62 | 53.12 |
| 9 | 37.21 | 51.97 | 33.60 | 38.30 | 33.67 | 30.46 | 36.87 | 23.43 | 56.29 |
| 10 | 30.72 | 50.00 | 30.15 | 33.82 | 32.64 | 23.53 | 27.33 | 29.50 | 44.61 |

TABLE 4

Passive Application

| | Corresponding Array 1 | 2 | 3 | 4 | 4 | 5 | 6 | 8 | 9 |
|---|---|---|---|---|---|---|---|---|---|
| 1 | 49.32 | 49.32 | 49.32 | 16.35 | 41.17 | 16.35 | 16.35 | 41.17 | 41.17 |
| 2 | 40.95 | 40.95 | 40.95 | 22.39 | 34.37 | 22.39 | 22.39 | 34.37 | 34.37 |
| 3 | 27.86 | 27.86 | 27.86 | 35.07 | 22.33 | 35.07 | 35.07 | 22.33 | 22.33 |
| 4 | 23.05 | 23.05 | 23.05 | 22.48 | 13.19 | 22.48 | 22.48 | 13.19 | 13.19 |
| 5 | 37.15 | 37.15 | 37.15 | 23.37 | 12.53 | 23.37 | 23.37 | 12.53 | 12.53 |
| 6 | 29.58 | 29.58 | 29.58 | 23.13 | 11.02 | 23.13 | 23.13 | 11.02 | 11.02 |
| 7 | 25.56 | 25.56 | 25.56 | 19.08 | 11.80 | 19.08 | 19.08 | 11.80 | 11.80 |
| 8 | 27.42 | 27.42 | 27.42 | 15.90 | 14.32 | 15.90 | 15.90 | 14.32 | 14.32 |
| 9 | 5.59 | 5.59 | 5.59 | 15.63 | 7.24 | 15.63 | 15.63 | 7.24 | 7.24 |
| 10 | 0.04 | 0.04 | 0.04 | 0.47 | 0.09 | 0.47 | 0.47 | 0.09 | 0.09 |

TABLE 2

| Array | | Thickness (mm) | Pitch (mm) | Poles per 25.4 cm | Magnetic Field Strength (mT) |
|---|---|---|---|---|---|
| 1 | Uni-directional | 0.2 | 2.13 | 12 | 9.8 |
| 2 | Uni-directional | 0.4 | 2.13 | 12 | 16.3 |
| 3 | Uni-directional | 0.6 | 2.13 | 12 | 23.2 |
| 4 | Uni-directional | 1.1 | 2.13 | 12 | 27 |
| 5 | Uni-directional | 1.1 | 3.18 | 8 | 4-10 |
| 6 | Uni-directional | 1.1 | 1.49 | 17 | 19.8 |
| 7 | Uni-directional | 1.1 | 1.0 | 25 | 11.5 |
| 8 | Bi-directional | 1st layer: 0.6 | 1st layer: 2.13 | 1st layer: 12 | 1st layer: 23.2 |
| | | 2nd layer: 0.2 | 2nd layer: 1.49 | 2nd layer: 17 | 2nd layer: 9.8 |
| 9 | Bi-directional | 1st layer: 0.6 | 1st layer: 2.13 | 1st layer: 12 | 1st layer: 23.2 |
| | | 2nd layer: 0.2 | 2nd layer: 1.06 | 2nd layer: 25 | 2nd layer: 4-10 |

Table 5 shows the amount (ng/strip) of Pal-KTTKS (SEQ ID NO: 1) measured on ten tape strip samples from a second test subject after active application of a Pal-KTTKS (SEQ ID NO: 1) formulation using several of the arrays in Table 2. The array number shown in Table 5 corresponds to the array of the same number in Table 2. Table 6 shows the average amounts (ng/strip) of Pal-KTTKS (SEQ ID NO: 1) measured on ten tape strip samples from a first test subject after passive application of the same Pal-KTTKS (SEQ ID NO: 1) formulation using a finger. The array number shown in Table 6 indicates which array in Table 5 the passive application is being compared to. Active and passive application of the Pal-KTTKS (SEQ ID NO: 1) formulation, and tape stripping and analysis of the resulting samples was conducted according to the Tape Stripping method, and commenced at the conclusion of four days and 8 applications of the Pal-KTTKS (SEQ ID NO: 1) formulation (2 applications per day). Array #4 and Array #7 were each tested twice.

Table 7 shows the amount (ng/strip) of Pal-KTTKS (SEQ ID NO: 1) measured on ten tape strip samples from a third test subject after active application of a Pal-KTTKS (SEQ ID NO: 1) formulation using several of the arrays in Table 2. The array number shown in Table 7 corresponds to the array of the same number in Table 2. Table 8 shows the average amounts (ng/strip) of Pal-KTTKS (SEQ ID NO: 1) measured on ten tape strip samples from a first test subject after passive application of the same Pal-KTTKS (SEQ ID NO: 1) formulation using a finger. The array number shown in Table 8 indicates which array in Table 7 the passive application is being compared to. Active and passive application of the Pal-KTTKS (SEQ ID NO: 1) formulation, and tape stripping and analysis of the resulting samples was conducted according to the Tape Stripping method, and commenced at the conclusion of four days and 8 applications of the Pal-KTTKS (SEQ ID NO: 1) formulation (2 applications per day). Array #4 was tested twice.

TABLE 5

Active Application for Test Subject #2

| | Array | | | | | | | | | |
|---|---|---|---|---|---|---|---|---|---|---|
| | 1 | 2 | 3 | 4 | 4 | 5 | 6 | 7 | 7 | 9 |
| 1 | 76.41 | 148.76 | 187.34 | 143.27 | 73.85 | 80.05 | 66.63 | 147.51 | 49.89 | 274.82 |
| 2 | 54.30 | 96.01 | 125.89 | 51.26 | 42.10 | 35.19 | 37.58 | 82.13 | 32.67 | 196.94 |
| 3 | 52.26 | 86.48 | 110.76 | 40.60 | 29.31 | 49.58 | 78.62 | 65.63 | 15.36 | 120.05 |
| 4 | 48.35 | 54.30 | 78.75 | 37.47 | 22.68 | 30.88 | 73.91 | 49.00 | 25.87 | 123.15 |
| 5 | 57.60 | 61.43 | 88.62 | 37.70 | 21.36 | 33.85 | 47.22 | 44.25 | 24.98 | 68.88 |
| 6 | 37.03 | 79.21 | 84.18 | 22.65 | 26.01 | 29.49 | 47.82 | 36.69 | 20.32 | 25.76 |
| 7 | 41.96 | 64.48 | 74.48 | 61.16 | 26.04 | 29.59 | 22.08 | 27.44 | 13.69 | 5.39 |
| 8 | 37.39 | 52.42 | 71.79 | 47.56 | 25.65 | 42.94 | 33.23 | 17.97 | 18.69 | 53.82 |
| 9 | 48.08 | 46.36 | 55.40 | 43.19 | 20.84 | 34.00 | 25.30 | 36.57 | 14.47 | 5.32 |
| 10 | 50.53 | 58.95 | 67.46 | 24.47 | 20.63 | 34.38 | 12.89 | 17.97 | 15.35 | 5.12 |

TABLE 6

Passive Application for Test Subject #2

| | Corresponding Array | | | | | | | | | |
|---|---|---|---|---|---|---|---|---|---|---|
| strip | 1 | 2 | 3 | 4 | 4 | 5 | 6 | 7 | 7 | 9 |
| 1 | 79.15 | 79.00 | 79.00 | 54.19 | 65.62 | 79.15 | 79.15 | 65.62 | 54.19 | 91.46 |
| 2 | 25.05 | 49.04 | 49.04 | 42.07 | 20.19 | 25.05 | 25.05 | 20.19 | 42.07 | 5.91 |
| 3 | 1.57 | 32.82 | 32.82 | 27.06 | 0.51 | 1.57 | 1.57 | 0.51 | 27.06 | 16.15 |
| 4 | 6.18 | 32.53 | 32.53 | 16.96 | 7.33 | 6.18 | 6.18 | 7.33 | 16.96 | 8.23 |
| 5 | 0.17 | 38.10 | 38.10 | 20.57 | 11.52 | 0.17 | 0.17 | 11.52 | 20.57 | 5.39 |
| 6 | 12.08 | 35.30 | 35.30 | 15.92 | 6.39 | 12.08 | 12.08 | 6.39 | 15.92 | 11.76 |
| 7 | 12.57 | 40.89 | 40.89 | 10.45 | 5.21 | 12.57 | 12.57 | 5.21 | 10.45 | 22.47 |
| 8 | 14.11 | 39.07 | 39.07 | 4.99 | 6.57 | 14.11 | 14.11 | 6.57 | 4.99 | 5.59 |
| 9 | 9.61 | 29.03 | 29.03 | 11.68 | 4.74 | 9.61 | 9.61 | 4.74 | 11.68 | 5.42 |
| 10 | 12.86 | 18.51 | 18.51 | 8.84 | 7.45 | 12.86 | 12.86 | 7.45 | 8.84 | 5.22 |

TABLE 7

Active Application for Test Subject #3

| strip | \multicolumn{9}{c}{Array} | | | | | | | | |
|---|---|---|---|---|---|---|---|---|---|
| | 1 | 2 | 3 | 4 | 4 | 5 | 6 | 7 | 8 | 9 |
| 1 | 180.96 | 87.78 | 41.15 | 101.60 | 46.93 | 30.35 | 47.37 | 209.62 | 46.42 | 59.76 |
| 2 | 158.86 | 72.34 | 56.25 | 80.32 | 27.46 | 619.23 | 46.55 | 172.48 | 44.20 | 62.74 |
| 3 | 149.31 | 73.97 | 60.85 | 90.50 | 27.44 | 322.26 | 72.34 | 187.98 | 41.37 | 55.25 |
| 4 | 166.70 | 65.52 | 55.34 | 82.01 | 24.76 | 195.47 | 66.29 | 185.07 | 46.80 | 53.81 |
| 5 | 182.66 | 69.46 | 48.97 | 84.48 | 24.36 | 25.48 | 23.87 | 172.13 | 35.94 | 45.48 |
| 6 | 159.00 | 82.45 | 39.54 | 98.82 | 23.21 | 4.78 | 41.92 | 187.40 | 34.93 | 44.70 |
| 7 | 140.35 | 63.67 | 55.15 | 83.27 | 25.02 | 5.10 | 30.77 | 176.71 | 34.48 | 38.11 |
| 8 | 190.78 | 74.85 | 52.95 | 85.83 | 21.54 | 147.68 | 35.00 | 142.37 | 26.94 | 46.29 |
| 9 | 134.01 | 71.91 | 46.83 | 85.16 | 16.63 | 30.04 | 24.48 | 171.43 | 13.01 | 36.70 |
| 10 | 152.16 | 74.08 | 30.52 | 75.04 | 15.28 | 41.43 | 45.18 | 178.87 | 10.11 | 39.72 |

TABLE 8

Passive Application for Test Subject #3

| strip | Corresponding Array | | | | | | | | | |
|---|---|---|---|---|---|---|---|---|---|---|
| | 1 | 2 | 3 | 4 | 4 | 5 | 6 | 7 | 8 | 9 |
| 1 | 188.13 | 49.17 | 31.64 | 49.17 | 32.55 | 179.06 | 31.64 | 188.13 | 32.55 | 32.55 |
| 2 | 157.66 | 39.50 | 28.92 | 39.50 | 28.14 | 44.86 | 28.92 | 157.66 | 28.14 | 28.14 |
| 3 | 161.29 | 38.06 | 23.16 | 38.06 | 27.78 | 116.86 | 23.16 | 161.29 | 27.78 | 27.78 |
| 4 | 143.20 | 37.52 | 20.62 | 37.52 | 32.27 | 140.42 | 20.62 | 143.20 | 32.27 | 32.27 |
| 5 | 102.85 | 19.72 | 26.14 | 19.72 | 27.05 | 103.88 | 26.14 | 102.85 | 27.05 | 27.05 |
| 6 | 112.49 | 14.11 | 37.90 | 14.11 | 26.40 | 53.64 | 37.90 | 112.49 | 26.40 | 26.40 |
| 7 | 122.71 | 39.03 | 36.62 | 39.03 | 23.07 | 13.11 | 36.62 | 122.71 | 23.07 | 23.07 |
| 8 | 120.11 | 36.50 | 34.54 | 36.50 | 22.06 | 79.01 | 34.54 | 120.11 | 22.06 | 22.06 |
| 9 | 132.60 | 44.38 | 28.51 | 44.38 | 15.64 | 18.60 | 28.51 | 132.60 | 15.64 | 15.64 |
| 10 | 145.23 | 55.49 | 27.32 | 55.49 | 14.75 | 61.48 | 27.32 | 145.23 | 14.75 | 14.75 |

Figure 5:
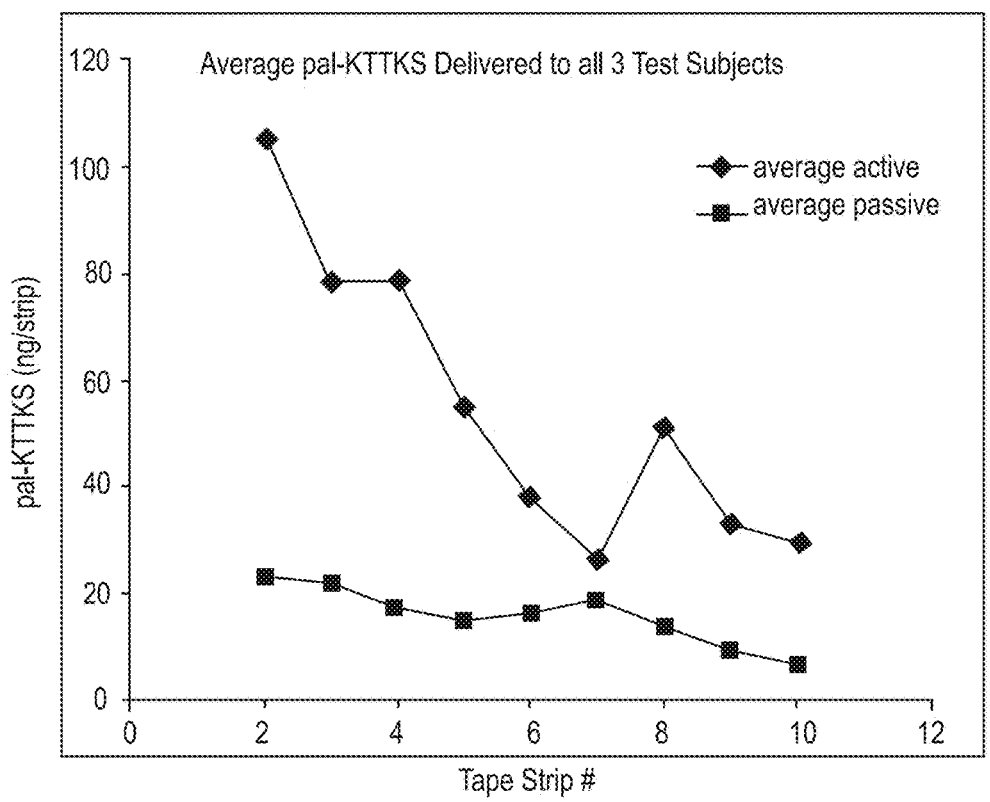
FIG. 5 is a plot of the enhanced penetration of Pal-KTTKS (SEQ ID NO: 1) using a magnetic array.

Magnetic array #9 demonstrated better penetration enhancement than some of the other magnetic arrays tested. The average Pal-KTTKS (SEQ ID NO: 1) actively and passively delivered to the three test subjects is plotted in the graph shown in FIG. 5. Table 9 shows the combined amount of Pal-KTTKS (SEQ ID NO: 1) measured on tape strips 2, 3 and 4; 5, 6 and 7; and 8, 9 and 10 for active application with bi-directional magnetic array #9 (as shown in Table 2) and the corresponding passive application. The combined amounts were averaged for test subject and strip. As shown in Table 9, active application resulted in significant enhanced delivery of Pal-KTTKS (SEQ ID NO: 1) compared to passive application.

TABLE 9

Magnetic Array #9

| combined strips | Subject | | | |
|---|---|---|---|---|
| | 1 | 2 | 3 | average |
| \multicolumn{5}{c}{Active Application} | | | | |
| s2-s4 | 177.13 | 440.14 | 171.79 | 263.02 |
| s5-s7 | 131.72 | 100.02 | 128.29 | 120.01 |
| s8-s10 | 154.03 | 64.27 | 122.70 | 113.67 |
| Mean | 154.29 | 201.48 | 140.93 | 165.57 |
| \multicolumn{5}{c}{Passive Application} | | | | |
| s2-s4 | 69.89 | 30.29 | 88.18 | 62.79 |
| s5-s7 | 35.35 | 39.62 | 76.52 | 50.50 |

TABLE 9-continued

Magnetic Array #9

| combined strips | Subject | | | |
|---|---|---|---|---|
| | 1 | 2 | 3 | average |
| s8-s10 | 21.64 | 16.23 | 52.45 | 30.11 |
| Mean | 42.29 | 28.71 | 72.39 | 47.80 |

Table 10 provides a statistical comparison of active delivery to passive delivery based on the average values shown in the last column of Table 9.

TABLE 10

| strips | p value | Enhancement (active/passive) |
|---|---|---|
| s2-s4 | 0.156 | 4.19 |
| S5-s7 | 0.0135 | 2.38 |
| S8-s10 | 0.0437 | 3.78 |

Figure 6:
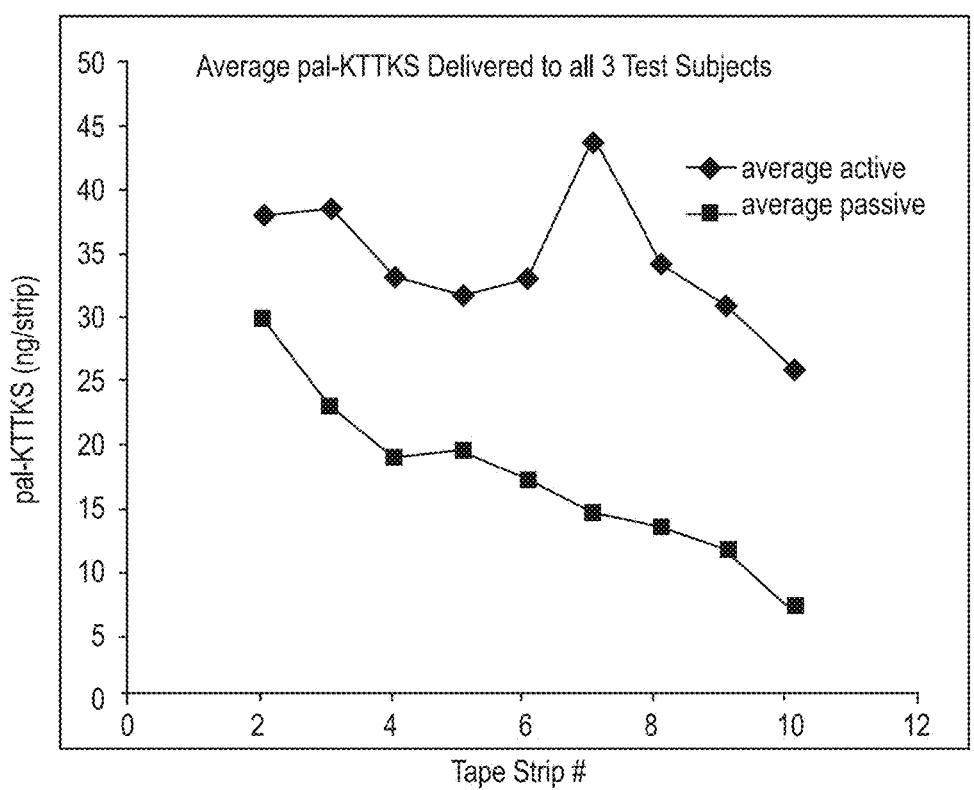
FIG. 6 is a plot of the enhanced penetration of Pal-KTTKS (SEQ ID NO: 1) using a magnetic array.

Magnetic array #4 also demonstrated better penetration enhancement than some of the other magnetic arrays tested. The average Pal-KTTKS (SEQ ID NO: 1) actively and passively delivered to the three test subjects is plotted in the graph shown in FIG. 6. Table 11 shows the combined amount of Pal-KTTKS (SEQ ID NO: 1) measured on tape strips 2, 3 and 4; 5, 6 and 7; and 8, 9 and 10 for active application with uni-directional magnetic array #4 (as shown in Table 2) and the corresponding passive application. The combined amounts were averaged for test subject and strip.

As shown in Table 11, active application resulted in significant enhanced delivery of Pal-KTTKS (SEQ ID NO: 1) compared to passive application.

TABLE 11

Magnetic Array # 4

| combined strips | Subject | | | | Average |
|---|---|---|---|---|---|
| | 1 | | 2 | 3 | |
| | Active Application | | | | |
| s2-s4 | 158.48 | 82.45 | 129.33 | 94.10 | 79.66 | 108.81 |
| s5-s7 | 154.85 | 117.42 | 121.51 | 73.41 | 72.59 | 107.95 |
| s8-s10 | 121.04 | 91.03 | 115.22 | 67.12 | 53.45 | 89.57 |
| Mean | 144.79 | 96.97 | 122.02 | 78.21 | 68.57 | 102.11 |
| | Passive Application | | | | |
| s2-s4 | 79.94 | 69.89 | 86.09 | 28.02 | 88.18 | 70.42 |
| s5-s7 | 65.58 | 35.35 | 46.95 | 23.11 | 76.52 | 49.50 |
| s8-s10 | 32.01 | 21.64 | 25.51 | 18.76 | 52.45 | 30.08 |
| Mean | 59.18 | 42.29 | 52.85 | 23.30 | 72.39 | 50.00 |

Table 12 provides a statistical comparison of active delivery to passive delivery based on the average values shown in the last column of Table 11.

TABLE 12

| strips | p value | Enhancement (active/passive) |
|---|---|---|
| s2-s4 | 0.0760 | 1.54 |
| S5-s7 | 0.0132 | 2.18 |
| S8-s10 | 0.0034 | 2.98 |

Example 3—Pal-KTTKS (SEQ ID NO: 1) In Vivo Skin Penetration Study #2

This in vivo skin penetration study compares the penetration of Pal-KTTKS (SEQ ID NO: 1) into skin when a Pal-KTTKS (SEQ ID NO: 1)-containing composition is applied with a magnetic applicator (active application) versus application with a non-magnetic applicator (passive application). In this example, 5 test subjects (A to E in Tables 13 and 14) were selected. 18 mg of a composition containing Pal-KTTKS (SEQ ID NO: 1) (Olay® Deep Wrinkle Treatment® brand skin cream available from the Procter & Gamble Company, Cincinnati, Ohio) was applied to two 3 cm×3 cm test sites on the inner forearms of each test subject using the applicator illustrated in FIG. 1C. The applicator used for active application included Array #8 from Table 2. The applicator used for passive application was the same as the one used for active application except without the magnetic array. Each forearm included an active application test site and a passive application site for a total of 10 active test sites and 10 passive sites. The application time was 30 seconds with a speed of motion of approximately 3 cm per second, equating to a gentle rubbing action. Application of the composition was followed by a 30 minute absorption period. The results of the passive and active application are shown in Tables 13 and 14 below. Penetration of Pal-KTTKS (SEQ ID NO: 1) was determined according to the Tape Stripping Method. The level of Pal-KTTKS (SEQ ID NO: 1) recovered from each tape strip was measured using HPLC and normalized to the total protein level measured on the tape strip.

Figure 7:
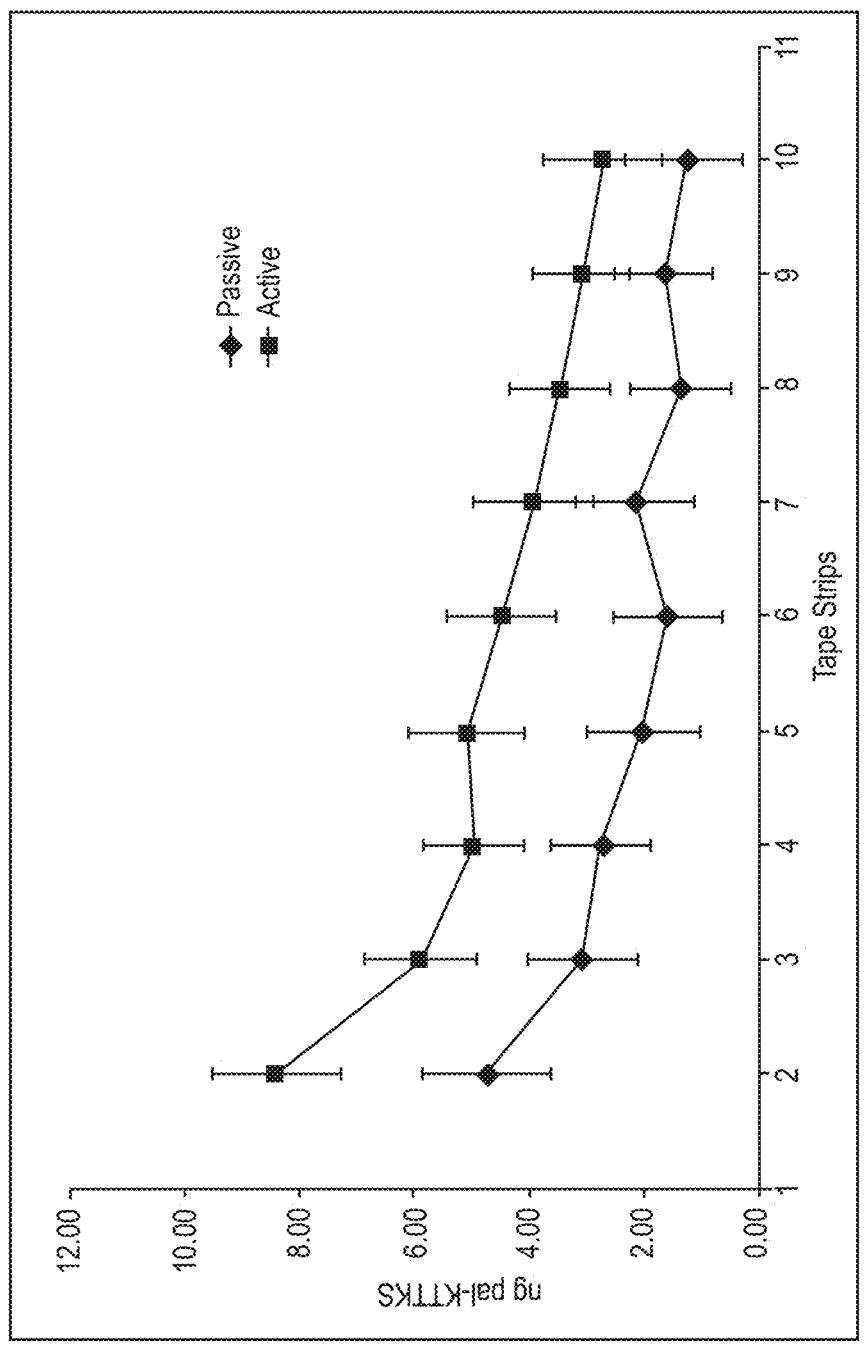
FIG. 7 is a plot of active versus passive application of Pal-KTTKS (SEQ ID NO: 1).

Tables 13 and 14 show the amount of Pal-KTTKS (SEQ ID NO: 1) recovered from each tape strip. Table 13 shows the results of applying the composition using a non-magnetic applicator, and Table 14 shows the results of applying the composition with a magnetic applicator configured to enhance penetration of Pal-KTTKS (SEQ ID NO: 1). The average value across all test sites is shown in the second to last cell of the row. The standard error of the mean (SEM) is shown in the last column of Tables 13 and 14. The SEM is calculated by dividing the standard deviation by the square root of the number of test sites. The active versus passive application results from Tables 13 and 14 are graphically illustrated in FIG. 7.

TABLE 13

Passive Application

| | Test Subject A | | Test Subject B | | Test Subject C | | Test Subject D | | Test Subject E | | | |
|---|---|---|---|---|---|---|---|---|---|---|---|---|
| | Site 1 | Site 2 | Site 1 | Site 2 | Site 1 | Site 2 | Site 1 | Site 2 | Site 1 | Site 2 | Avg | SEM |
| 1 | 11.87 | 1.77 | 8.98 | 0.00 | 15.35 | 11.18 | 6.90 | 15.05 | 8.02 | 6.31 | 8.54 | 1.61 |
| 2 | 7.83 | 0.00 | 5.94 | 5.32 | 4.08 | 9.21 | 4.51 | 5.44 | 1.66 | 3.51 | 4.75 | 0.85 |
| 3 | 6.62 | 0.00 | 2.46 | 3.17 | 2.68 | 7.90 | 1.44 | 2.37 | 1.77 | 2.16 | 3.06 | 0.76 |
| 4 | 7.56 | 2.45 | 1.93 | 1.08 | 1.83 | 8.33 | 1.22 | 0.00 | 1.27 | 1.76 | 2.74 | 0.89 |
| 5 | 7.02 | 0.00 | 1.39 | 1.04 | 0.00 | 7.60 | 1.29 | 0.00 | 0.80 | 1.09 | 2.02 | 0.90 |
| 6 | 6.46 | 0.00 | 0.86 | 0.00 | 0.00 | 7.45 | 0.00 | 0.00 | 0.39 | 0.65 | 1.58 | 0.90 |
| 7 | 6.98 | 0.00 | 0.00 | 0.00 | 3.40 | 7.75 | 2.06 | 0.00 | 0.52 | 0.58 | 2.13 | 0.94 |
| 8 | 6.75 | 0.00 | 0.00 | 0.00 | 0.00 | 6.68 | 0.00 | 0.00 | 0.00 | 0.00 | 1.34 | 0.90 |
| 9 | 6.60 | 0.00 | 0.00 | 0.00 | 2.16 | 7.62 | 0.00 | 0.00 | 0.00 | 0.00 | 1.64 | 0.94 |
| 10 | 6.58 | 0.00 | 0.00 | 0.00 | 0.00 | 6.32 | 0.00 | 0.00 | 0.00 | 0.00 | 1.29 | 0.86 |
| Sum 2-10 | 62.40 | 2.45 | 12.58 | 10.61 | 14.16 | 68.87 | 10.53 | 7.81 | 6.41 | 9.74 | 20.55 | 7.60 |
| Sum 6-10 | 40.39 | 0.00 | 2.25 | 1.04 | 5.56 | 43.44 | 3.35 | 0.00 | 1.72 | 2.31 | 10.01 | 5.35 |

TABLE 14

Active Application

| | Test Subject A | | Test Subject B | | Test Subject C | | Test Subject D | | Test Subject E | | | |
|---|---|---|---|---|---|---|---|---|---|---|---|---|
| | Site 1 | Site 2 | Site 1 | Site 2 | Site 1 | Site 2 | Site 1 | Site 2 | Site 1 | Site 2 | Avg | SEM |
| 1 | 15.33 | 2.41 | 15.52 | 24.11 | 8.97 | 15.20 | 6.49 | 13.55 | 12.28 | 13.73 | 12.76 | 1.86 |
| 2 | 10.60 | 8.89 | 10.74 | 10.58 | 4.67 | 15.66 | 4.28 | 5.70 | 5.94 | 7.16 | 8.42 | 1.12 |
| 3 | 9.50 | 8.28 | 5.95 | 6.45 | 4.17 | 11.45 | 2.20 | 2.78 | 3.85 | 4.27 | 5.89 | 0.96 |
| 4 | 9.52 | 5.95 | 4.62 | 2.86 | 3.40 | 9.11 | 2.36 | 1.80 | 6.52 | 3.51 | 4.96 | 0.86 |
| 5 | 9.54 | 4.20 | 5.81 | 5.35 | 2.53 | 11.04 | 1.78 | 1.87 | 5.05 | 3.61 | 5.08 | 0.98 |
| 6 | 9.75 | 3.74 | 4.53 | 0.95 | 2.72 | 9.58 | 2.42 | 2.01 | 5.05 | 3.97 | 4.47 | 0.95 |
| 7 | 9.73 | 2.37 | 3.71 | 3.22 | 2.25 | 10.34 | 2.01 | 1.45 | 2.71 | 1.43 | 3.92 | 1.04 |
| 8 | 8.16 | 3.18 | 3.38 | 4.89 | 3.20 | 7.92 | 1.59 | 0.00 | 0.53 | 1.88 | 3.47 | 0.89 |
| 9 | 8.07 | 2.51 | 1.99 | 2.55 | 3.43 | 7.87 | 0.99 | 1.41 | 1.07 | 0.95 | 3.08 | 0.85 |
| 10 | 8.56 | 1.29 | 1.94 | 0.00 | 5.27 | 7.91 | 0.47 | 1.28 | 0.45 | 0.00 | 2.72 | 1.04 |
| Sum 2-10 | 83.43 | 40.40 | 42.67 | 36.84 | 31.64 | 90.87 | 18.10 | 18.31 | 31.17 | 26.78 | 42.02 | 7.97 |
| Sum 6-10 | 53.81 | 17.29 | 21.36 | 16.95 | 19.40 | 54.66 | 9.26 | 8.02 | 14.86 | 11.84 | 22.74 | 5.42 |

Table 15 compares the results of active application versus passive application based on the additive amounts of Pal-KTTKS (SEQ ID NO: 1) recovered from tape strips 2 to 10 and 6 to 10. The enhancement values shown in Table 15 are calculated by dividing the active value from Table 14 by the passive value from Table 13. The average shown in the last column of Table 15 is calculated by averaging the enhancement values of all the test sites. In instances where the passive value from Table 13 was zero, resulting in a divide-by-zero situation, the enhancement value is not included for purposes of the average. The p-value is calculated using a paired t-test. As shown in Table 15, active application of the composition delivered an average of 4× as much Pal-KTTKS (SEQ ID NO: 1) into the skin compared to passive application according to tape strips 2-10, and over 6× as much when according to tape strips 6-10. This suggests that the specific magnetic applicator used in this example can drive Pal-KTTKS (SEQ ID NO: 1) deeper into the skin where it can provide an improved skin care benefit.

Coefficient of friction is the ratio of the force of friction between two bodies and the force pressing them together. The instrument used to determine the coefficient of friction is a Bruker® UMT-2 tribometer or equivalent. A purple nitrile glove is used as one of the two materials in the test. The other material used in the test is the test surface (e.g., skin contacting surface of the applicator or cover). The purple nitrile glove material is placed over the probe of the tribometer. The test surface to be measured is placed in contact with the nitrile-covered probe of the instrument, and the force is measured according to the manufacturer's operating instructions for the instrument.

FIG. 8 illustrates the system 900 used to measure coefficient of friction in this example. As shown in FIG. 8, a probe 902 covered with purple nitrile glove material is contacted with the skin-contacting surface 920 of an applicator 910. In this example, the cover has been removed from the applicator 910 and the magnetic array provides the skin-contacting surface 920. The skin-contacting surface of the cover (not shown) was also measured. Both the appli-

TABLE 15

Comparison of Active v. Passive Application

| | Test Subject A | | Test Subject B | | Test Subject C | | Test Subject D | | Test Subject E | | | |
|---|---|---|---|---|---|---|---|---|---|---|---|---|
| | Site 1 | Site 2 | Site 1 | Site 2 | Site 1 | Site 2 | Site 1 | Site 2 | Site 1 | Site 2 | Avg | P-value |
| Enhancement value Strips 2-10 | 1.34 | 16.52 | 3.39 | 3.47 | 2.23 | 1.32 | 1.72 | 2.35 | 4.86 | 2.75 | 4.00 | $3.533 \times 10^{-5}$ |
| Enhancement value Strips 6-10 | 1.33 | — | 18.16 | — | 3.03 | 1.22 | 3.63 | — | 10.70 | 6.73 | 6.40 | $4.526 \times 10^{-6}$ |

Example 4—Coefficient of Friction

Coefficient of Friction Method

This method provides a means to determine the coefficient of friction of material surfaces herein. Wet coefficient of friction refers to the coefficient of friction measured on a surface on which a skin care composition is present. Dry coefficient of friction refers to the coefficient of friction measured on a surface on which a skin care composition is not present.

cator surface 920 and the cover were tested with and without a skin care composition (Olay® Deep Wrinkle Treatment® brand skin cream available from the Procter & Gamble Co., Ohio). For measuring wet coefficient of friction, 0.1 g of the skin care composition was spread over the test surface. The rate of the probe was set to 1 mm/sec with a force of 100 grams.

Each leg of the test was repeated three times. The coefficient of friction results are shown in Table 16 below.

TABLE 16

| Surface | Coefficient of Friction | | | |
| --- | --- | --- | --- | --- |
| | 1 | 2 | 3 | Avg. |
| Applicator surface (dry) | 1.90 | 1.97 | 1.86 | 1.91 |
| Applicator surface (wet) | 0.45 | 0.62 | 0.45 | 0.50 |
| Cover surface (dry) | 0.77 | 0.96 | 1.09 | 0.94 |
| Cover surface (wet) | 0.06 | 0.06 | 0.06 | 0.06 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cosmetic skin care product, comprising:
   a. an applicator comprising a substrate with a magnetic array embedded therein, the magnetic array comprising a first layer of dipole pairs of alternating magnetic poles with a pitch of between 1.7 and 2.5 and a magnetic field strength of between about 24.0 and 36.0 mT, and a second layer of dipole pairs of alternating magnetic poles having a thickness of between about 0.05 mm and about 0.5 mm, wherein the magnetized substrate enhances penetration of pal-KTTKS (SEQ ID NO: 1) into skin; and
   b. a skin care composition comprising Pal-KTTKS (SEQ ID NO: 1) and a dermatologically acceptable carrier.

2. The skin care product of claim 1, wherein the first layer has a thickness of between 0.8 and 1.2 mm.

3. The skin care product of claim 1, wherein the magnetic array enhances delivery of the Pal-KTTKS (SEQ ID NO: 1) by at least 1.5 times better than an applicator that does not include the magnetic array.

4. The skin care product of claim 3, wherein the magnetic array enhances delivery of the Pal-KTTKS (SEQ ID NO: 1) as measured in tape strips 2 to 10 according to the Tape Strip Method.

5. The skin care product of claim 1, wherein the substrate further comprises a ferromagnetic material.

6. The skin care product of claim 5, wherein the ferromagnetic material is selected from iron, iron containing materials, cobalt, cobalt containing materials, strontium, strontium containing materials, barium, barium containing materials, nickel, nickel containing materials, alloys and oxides of these and combinations thereof.

7. The skin care product of claim 1, wherein the substrate comprises boron, carbon, silicon, phosphorous, aluminum, neodymium, samarium or a combination of these.

8. The skin care product of claim 1, wherein the magnetic substrate includes a skin facing side and a distal side opposed thereto, and a magnetic return is provided at the distal side.

9. The skin care product of claim 1, wherein the applicator further comprises a cover that covers a skin facing surface of the applicator.

10. The skin care product of claim 9, wherein the cover comprises a surface having a dry coefficient of friction that is at least 10% less than the skin facing surface of the applicator according to the Friction Test.

11. The skin care product of claim 1, wherein the magnetic array includes a second layer of at least one dipole pair of alternating magnetic poles, and wherein the second layer has a pitch and a magnetic field strength that are both less than or equal to the pitch and magnetic field strength of the first layer.

12. The skin care product of claim 11, wherein the second layer has a pitch of between 0.8 and 1.3.

13. The skin care product of claim 11, wherein the second layer has a magnetic field strength of between about 1 and 20 mT.

14. The skin care product of claim 11, wherein the first layer is angularly offset from the second layer to form a bi-directional magnetic array.

15. The skin care product of claim 14, wherein the first and second layers are angularly offset by about 90 degrees.

16. The skin care product of claim 1, wherein the applicator and the skin care composition are packaged in separate packages, which are joined to one another, and at least one of the applicator package and the skin care composition package includes indicia that non-verbally communicate to a user that the magnetic array enhances penetration of the Pal-KTTKS (SEQ ID NO: 1).

* * * * *

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: palmitoyl-
      lys-thr-thr-lys-ser

<400> SEQUENCE: 1

Lys Thr Thr Lys Ser
1               5
```